US008764850B2

(12) United States Patent
Hansen et al.

(10) Patent No.: US 8,764,850 B2
(45) Date of Patent: Jul. 1, 2014

(54) BI-MODAL ANKLE-FOOT DEVICE

(75) Inventors: Andrew H. Hansen, Round Lake, IL (US); Dudley S. Childress, Wilmette, IL (US)

(73) Assignee: Northwestern University, Evanston, IL (US)

( * ) Notice: Subject to any disclaimer, the term of this patent is extended or adjusted under 35 U.S.C. 154(b) by 848 days.

(21) Appl. No.: 12/462,056

(22) Filed: Jul. 28, 2009

(65) Prior Publication Data

US 2010/0030343 A1  Feb. 4, 2010

Related U.S. Application Data

(60) Provisional application No. 61/137,765, filed on Jul. 31, 2008.

(51) Int. Cl.
*A61F 2/64* (2006.01)
*A61F 2/66* (2006.01)
A61F 2/72 (2006.01)
A61F 2/50 (2006.01)
A61F 2/30 (2006.01)
A61F 2/76 (2006.01)
A61F 2/68 (2006.01)
A61F 2/70 (2006.01)

(52) U.S. Cl.
CPC .............. *A61F 2/6607* (2013.01); *A61F 2/72* (2013.01); *A61F 2002/5075* (2013.01); *A61F 2002/30359* (2013.01); *A61F 2002/30476* (2013.01); *A61F 2002/7615* (2013.01); *A61F 2002/6845* (2013.01); *A61F 2002/6621* (2013.01); *A61F 2002/30492* (2013.01); *A61F 2002/701* (2013.01); *A61F 2002/5009* (2013.01); *A61F 2002/5043* (2013.01); *A61F 2/68* (2013.01); *A61F 2002/5055* (2013.01); *A61F 2002/5078* (2013.01); *A61F 2220/0025* (2013.01); *A61F 2002/6818* (2013.01); *A61F 2002/5041* (2013.01); *A61F 2002/5001* (2013.01); *A61F 2002/5056* (2013.01); *A61F 2002/5003* (2013.01); *A61F 2002/665* (2013.01); *A61F 2002/6854* (2013.01); *A61F 2220/0033* (2013.01)
USPC ............................................... 623/47

(58) Field of Classification Search
CPC ..................................... A61F 2/6607
USPC ..................................... 623/47–52
See application file for complete search history.

(56) References Cited

U.S. PATENT DOCUMENTS 5,443,528 A * 8/1995 Allen ............................ 623/52
5,728,175 A * 3/1998 Rincoe ........................... 623/49
(Continued)

FOREIGN PATENT DOCUMENTS

GB       2161386 A  * 1/1986 ............... A61F 2/64

OTHER PUBLICATIONS

Adamczyk, P.G., Collins, S.H. and Kuo, A.D., The advantages of a rolling foot in human walking. J. Exp. Biol., 209, pp. 3953-3963, 2006.

(Continued)

*Primary Examiner* — David Isabella
*Assistant Examiner* — Jacqueline Woznicki
(74) *Attorney, Agent, or Firm* — Cook Alex Ltd.

(57) ABSTRACT

A bi-modal ankle-foot device that provides a curved effective shape appropriate for walking and a flattened effective shape for standing. The bi-modal ankle-foot device includes a foot piece and a lockable ankle joint connected to the flat foot piece, the ankle joint and foot piece cooperating to provide a curved shape for walking when the ankle joint is unlocked and to provide a flattened shape for standing when the ankle joint is locked.

32 Claims, 15 Drawing Sheets

(56) References Cited

U.S. PATENT DOCUMENTS

| | | | | |
|---|---|---|---|---|
| 5,913,901 | A * | 6/1999 | Lacroix | 623/47 |
| 6,238,124 | B1 * | 5/2001 | Merlo | 403/93 |
| 6,500,138 | B1 * | 12/2002 | Irby et al. | 602/26 |
| 7,318,504 | B2 * | 1/2008 | Vitale et al. | 188/265 |
| 8,435,309 | B2 * | 5/2013 | Gilbert et al. | 623/39 |
| 2004/0054423 | A1 * | 3/2004 | Martin | 623/25 |
| 2004/0153168 | A1 * | 8/2004 | Childress et al. | 623/55 |
| 2004/0225375 | A1 * | 11/2004 | Chen | 623/38 |
| 2005/0109563 | A1 * | 5/2005 | Vitale et al. | 188/1.11 R |
| 2005/0137717 | A1 * | 6/2005 | Gramnas et al. | 623/38 |
| 2007/0270976 | A1 * | 11/2007 | DeHarde et al. | 623/27 |
| 2008/0114470 | A1 * | 5/2008 | Hill et al. | 623/38 |
| 2009/0299480 | A1 * | 12/2009 | Gilbert et al. | 623/18.11 |
| 2010/0030343 | A1 * | 2/2010 | Hansen et al. | 623/47 |
| 2010/0030344 | A1 * | 2/2010 | Hansen et al. | 623/53 |
| 2010/0263233 | A1 * | 10/2010 | Hansen et al. | 36/103 |
| 2013/0268093 | A1 * | 10/2013 | Gilbert et al. | 623/46 |

OTHER PUBLICATIONS

Collins, S., Ruina, A., Tedrake, R., Wisse, M., Efficient bipedal robots based on passive-dynamic walkers, Science, 307, pp. 1082-1085, 2005.

Gailey, R.S., Roach, K.E., Applegate, E.B., Cho, B., Lict, S., Maguire, M., and Nash, M.S., The amputee mobility predictor: an instrument to assess determinants of the lower-limb amputee's ability to ambulate, Arch. Phys. Med. Rehabil., 83, 613-627, 2002.

Gard, S.A. and Childress, D.S., What determines the vertical displacement of the body during normal walking?, J. Prosthet. Orthot., 13, pp. 64-67, 2001.

Hansen, A.H., Roll-over characteristics of human walking with applications for artificial limbs, Ph.D. thesis, Evanston, Northwestern University, Sep. 2006.

Hansen, A.H., Childress, D.S. and Knox, E.H., Roll-over shapes of human locomoter systems: effects of walking speed, Clin. Biomech., 19(4), pp. 407-414, 2004.

Hansen, A.H., Childress, D.S. and Miff, S.C., Roll-over characteristics of human walking on inclined surfaces, Hum. Movement Sci., 23(6), pp. 807-821, 2004.

Hansen, A., Sam, M., Childress, D., The effective foot length ratio: a potential tool for characterization and evaluation of prosthetic feet, J. Prosthet. Orthot., 16(2), pp. 41-45, 2004.

Hansen, A.H., and Childress, D.S., Effects of shoe heel height on biological rollover characteristics during walking, J. Rehabil. Res. Dev., 41(4), pp. 547-554, 2004.

Hansen, A.H., and Childress, D.S., Effects of adding weight to the torso on roll-over characteristics of walking, J. Rehabil. Res. Dev., 42(3), pp. 381-390, 2005.

Hullin, M.G. and Robb, J.E., Biomechanical effects of rockers on walking in a plaster cast, J. Bone Joint Surg. Br., 73(1), pp. 92-95, 1991.

McGreer, T., Passive dynamic walking, Int. J. Robot. Res., 9(2), pp. 62-82, 1990.

Miff, S.C., Hansen A.H., Childress, D.S., Gard, S.A., Meier, M.R., Roll-over shapes of the able-bodied knee-ankle-foot system during gait initiation, steady-state walking, and gait termination, Gait and Posture, 27, pp. 316-322, 2008.

Wisse, M. and Frankenhuyzen, J., Design and construction of MIKE; a 2-D autonomous biped based on passive dynamic walking, Proceedings of the AMAM Conference of Adaptive Motion of Animals and Machines, Kyoto, Japan, 2003.

\* cited by examiner

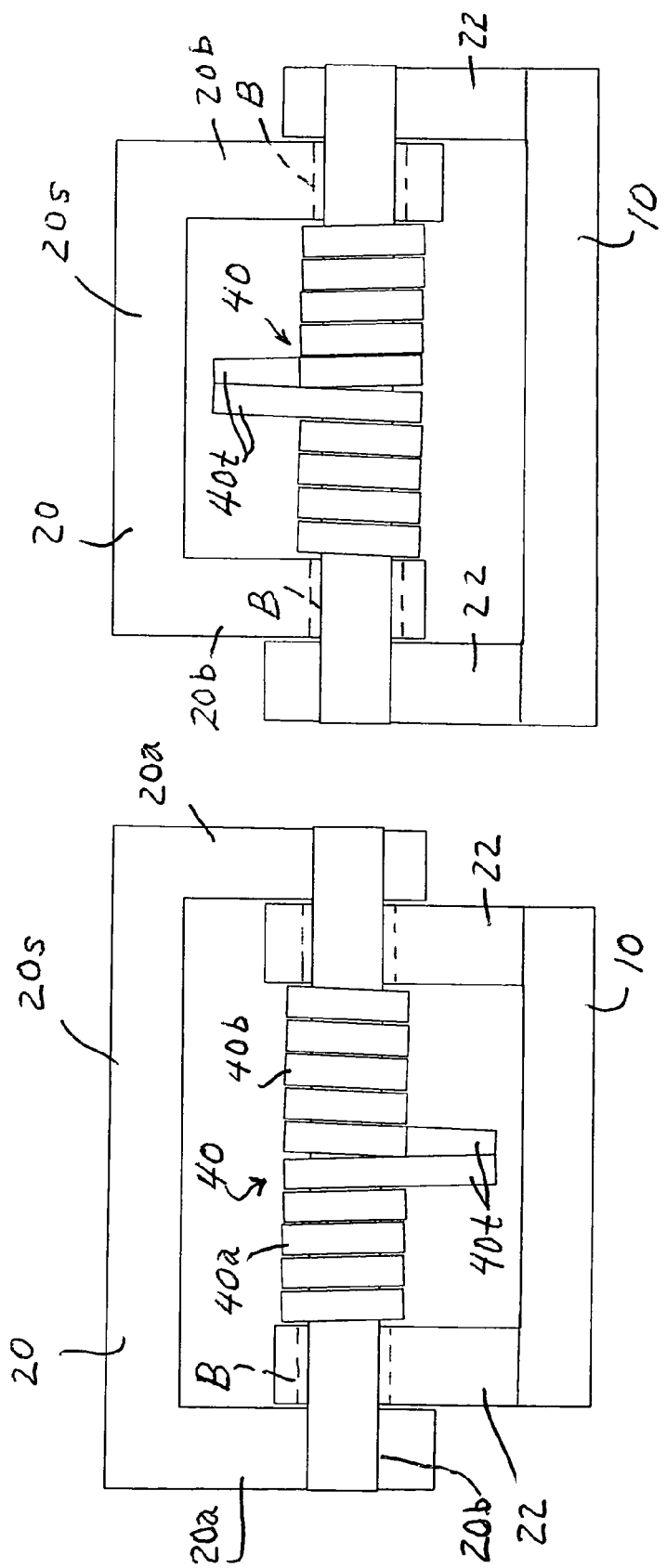

Unlocked Ankle

Locked Ankle

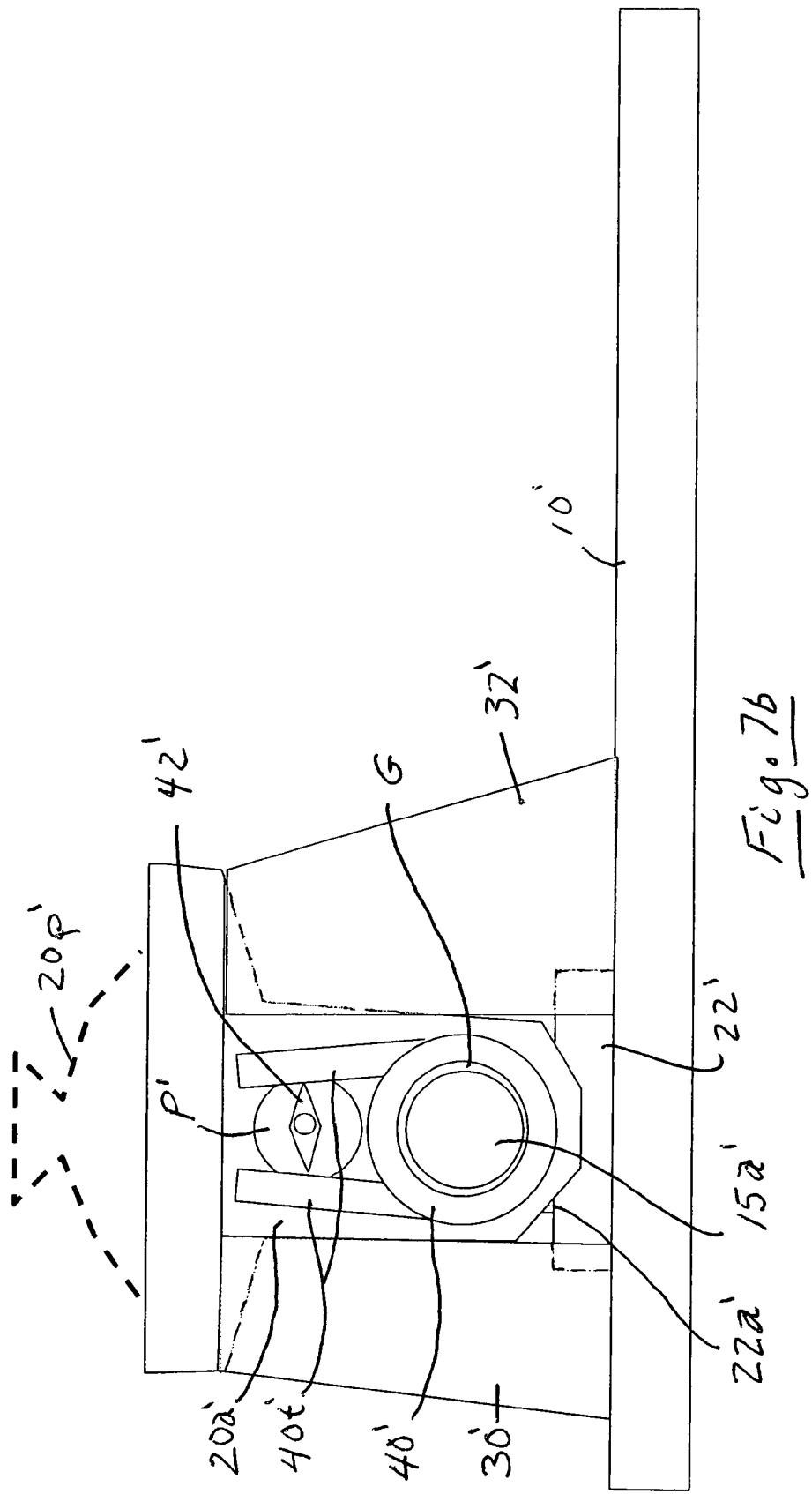

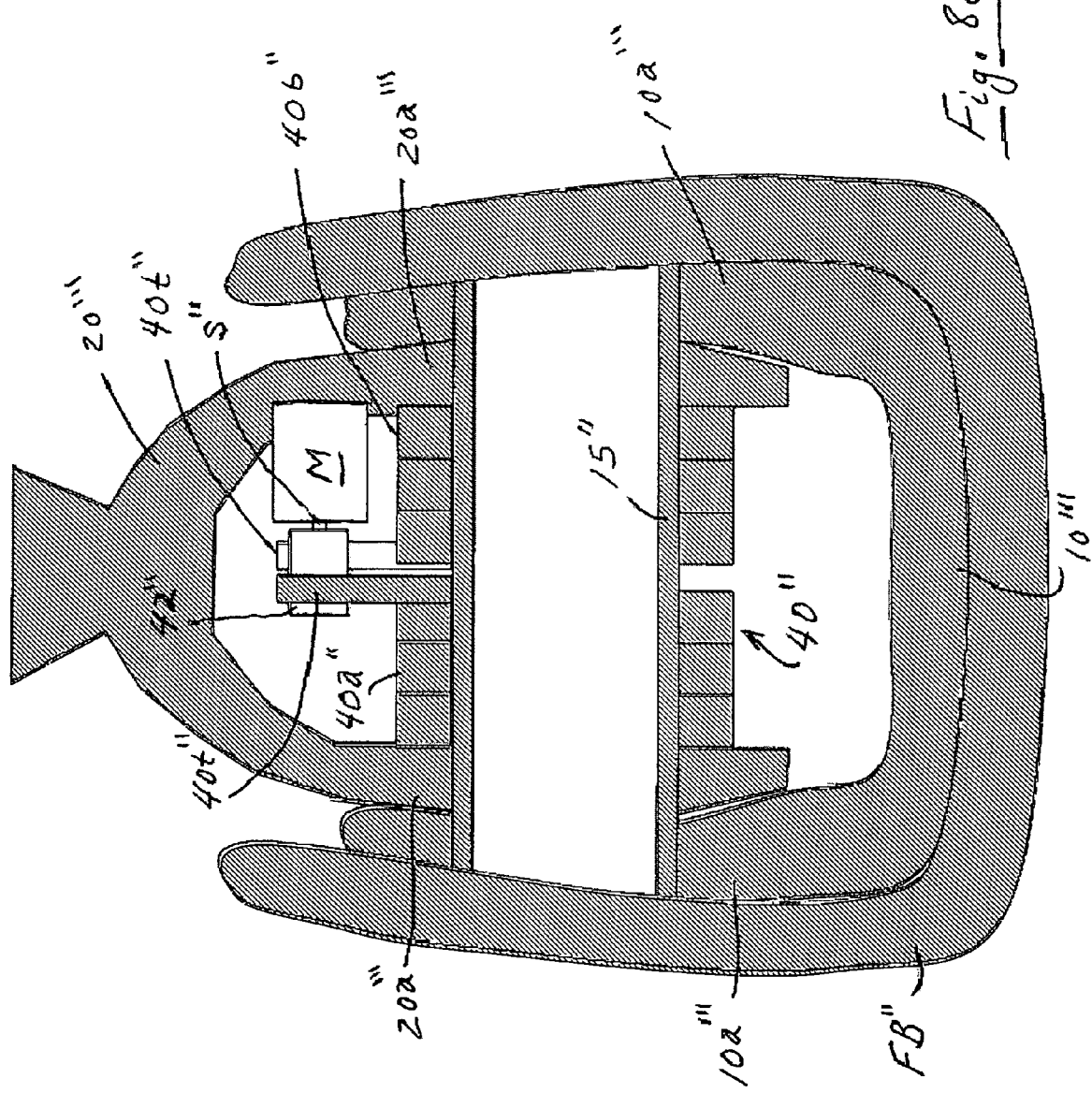

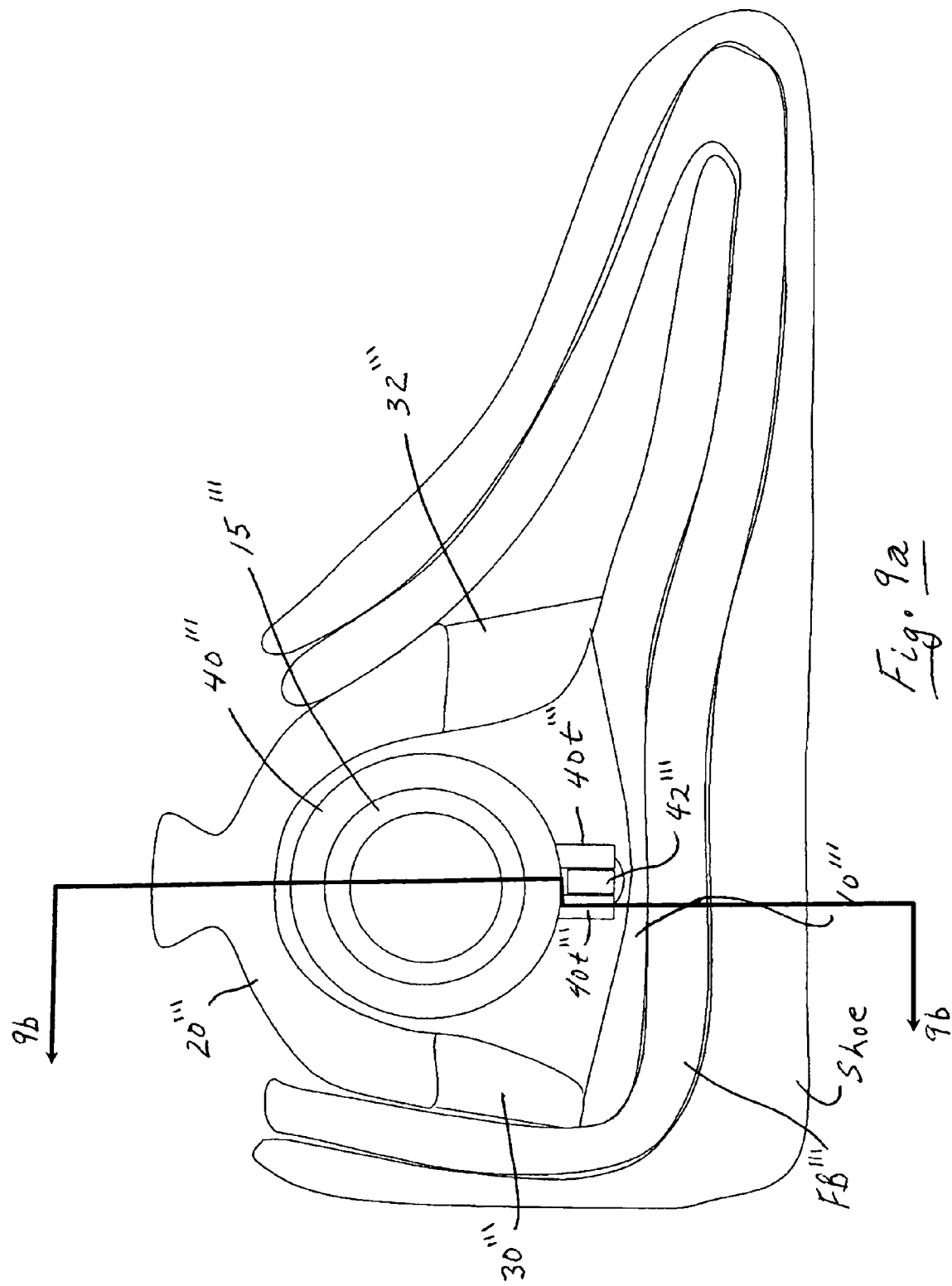

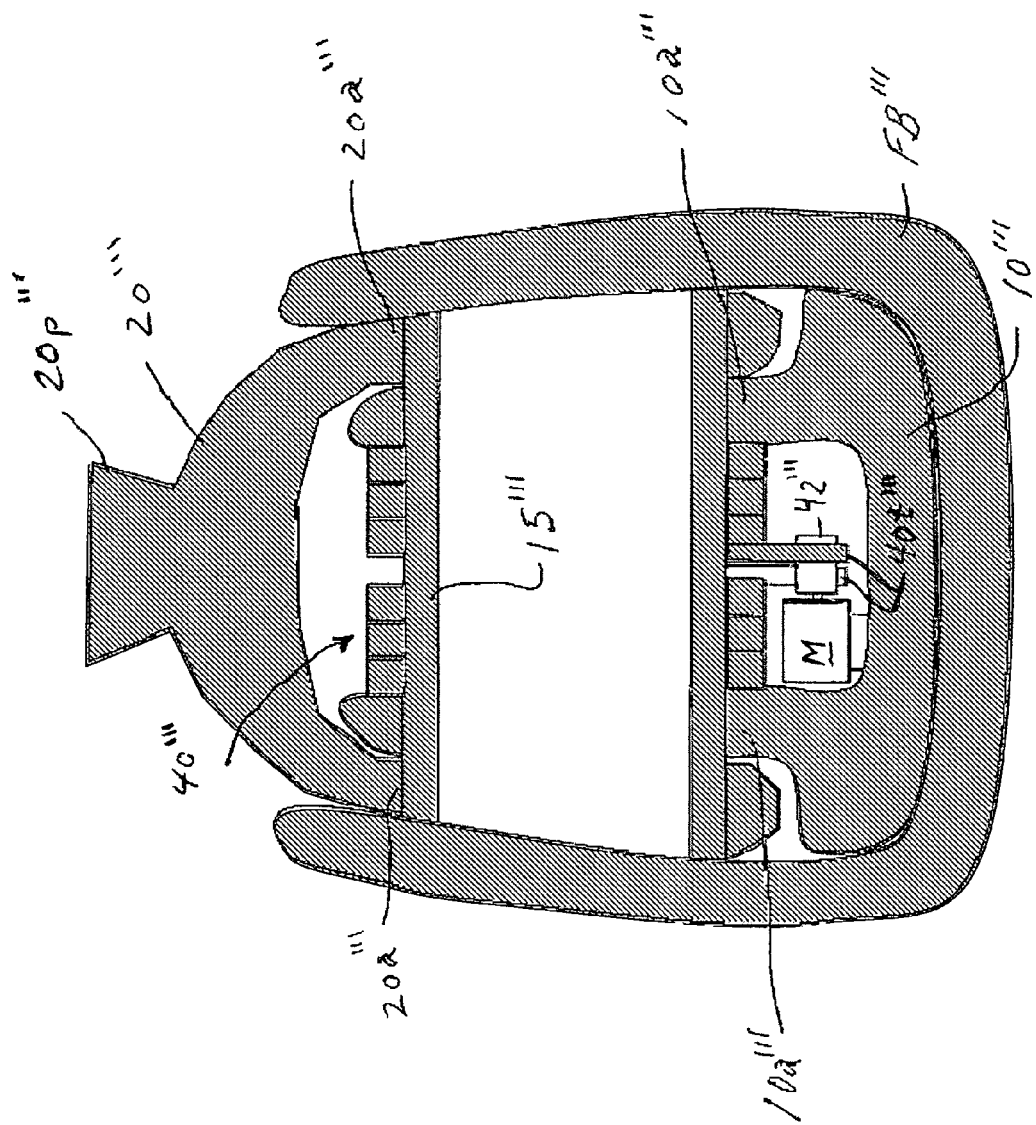

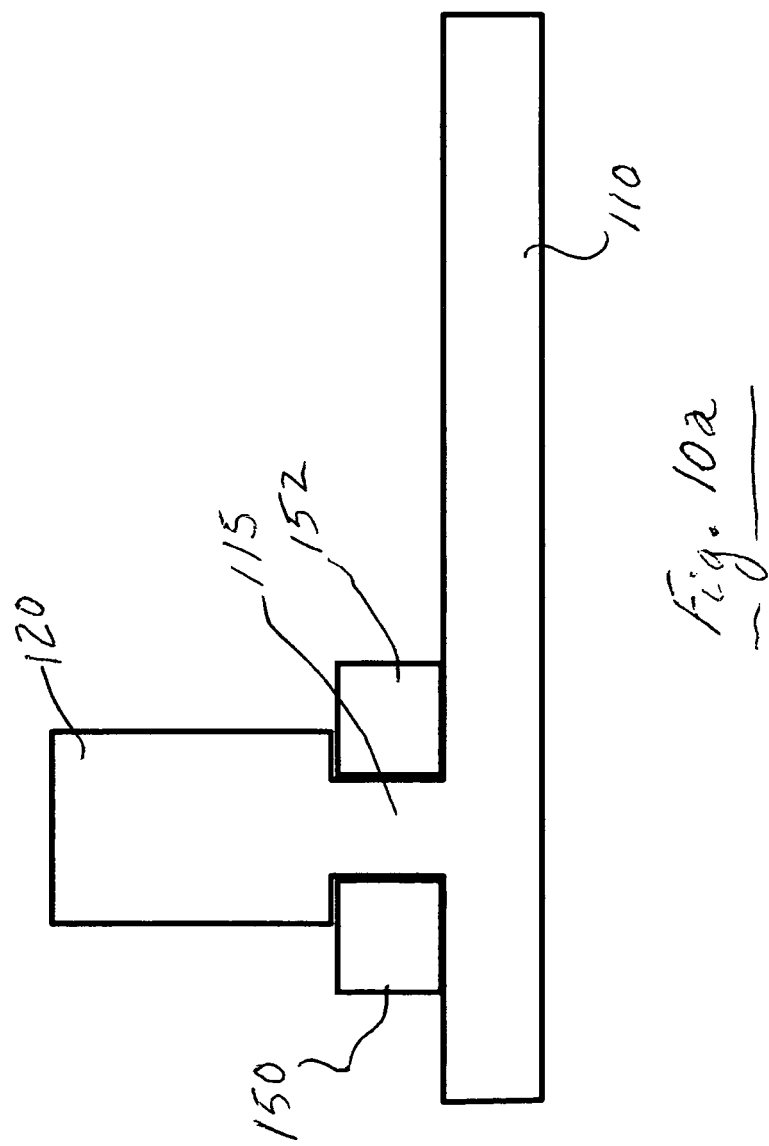

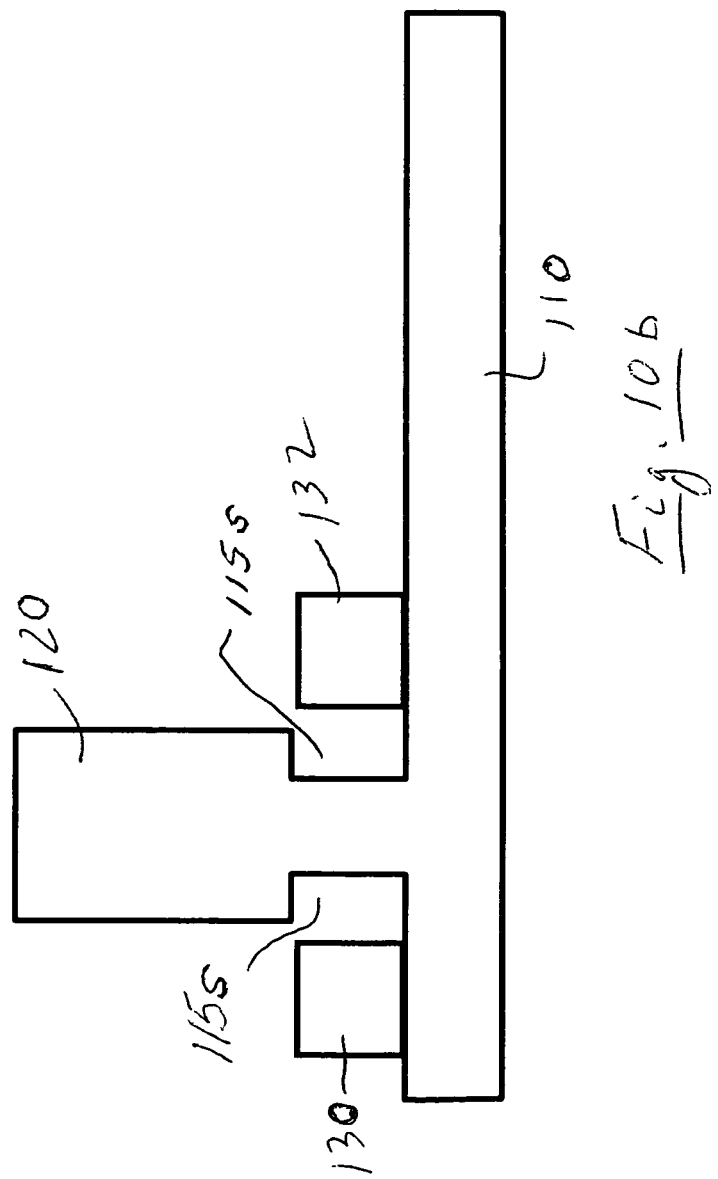

BI-MODAL ANKLE-FOOT DEVICE

This application claims benefits and priority of provisional application Ser. No. 61/137,765 filed Jul. 31, 2008, the entire disclosure of which is incorporated herein by reference.

CONTRACTUAL ORIGIN OF THE INVENTION

This invention was made with government support under Contract/Grant No. H133E030030 awarded by the National Institute on Disability and Rehabilitation Research (United States Department of Education) and under Contract/Grant No. RO3-HD050428-01A2 awarded by the National Institute of Health. The government has certain rights in the invention.

FIELD OF THE INVENTION

The present invention relates to a bi-modal ankle-foot device that can mimic the biological response of able-bodied persons during standing and walking and, more particularly, to a bi-modal ankle-foot prosthetic or orthotic device that provides a curved effective shape during walking and a flattened effective shape during standing.

BACKGROUND OF THE INVENTION

Clinical Significance

According to data from Adams et al. (1999), the prevalence of the absence of extremities (excluding tips of fingers or toes) was 1,285,000 in the U.S. in 1996. We know from the same sources that approximately 87% of limb amputations are the result of vascular disease. Scandinavian data (Soderberg et al., 2001) indicates that 90% of all lower-limb amputations result from dysvascular conditions, supporting the U.S. data. Meier (1998) has indicated that the majority of lower-limb amputees are more than 50 years of age and that the largest percentage has amputations because of vascular disease that is often associated with diabetes.

Owings and Kozak (1998) indicate that there were 185,000 surgical amputations amputations, toe amputations, and "other" amputations are removed from the data, we are left with 3,000 upper-limb amputations per year and 100,000 lower-limb amputations per year. If 87% of the lower-limb amputations are of vascular origin, about 87,000 amputations per year would be of this variety, leaving around 13,000 amputations per year mostly related to trauma. The limb loss group with vascular disease tends to be older while the group with trauma tends to be younger. Therefore, in the United States, it is highly likely that most of the prostheses fabricated each year are for K1 and K2 level amputees (see next paragraph for an explanation of the K levels), who may benefit substantially from a more stable ankle-foot prosthetic component. These estimates are based on data that are over ten years old. The older population has increased dramatically in the last ten years, making these estimates conservative.

In 1995, the Medicare Functional Classification Levels (MFCL) were developed to assess the functional abilities of persons with lower-limb amputation (Gailey et al., 2002). The MFCL has 5 level codes: K0, K1, K2, K3, and K4. The lowest level, K0, is for persons who would not benefit from the use of a prosthesis because they do not have the ability or potential to ambulate or transfer. Persons in this level do not receive a prosthesis. Level K1 is for persons who could use a prosthesis to transfer and ambulate on level terrain at a fixed rate. Most K1 level users are limited or unlimited household ambulators. Persons in level K2 are limited community ambulators, capable of minor terrain obstacles, but who cannot significantly vary their cadence. Levels K3 and K4 are reserved for amputees with potential for higher intensity use of their prostheses, with level K4 identifying extremely vigorous persons including athletes, children, and active adults. Unilateral amputees in the higher levels (K3 and K4) may not benefit from the added stability of a bi-modal ankle-foot system because they tend to have good balance and control over their prostheses and a sound limb to assist with balance deficits on the prosthetic side. However, unilateral prosthesis users at the lower functional levels (K1 and K2) and bilateral prosthesis users may have balance and control issues necessitating the use of assistive devices (e.g. canes or walkers). The use of a more stable prosthetic foot may allow them to ambulate without the assistive device or with less reliance on the device, reducing stress to the upper limb controlling the assistive device.

Miller et al. (2001) studied 435 daily users of lower limb prostheses to examine relationships between falling, fear of falling, and balance confidence on mobility and social activity outcomes. Their results indicated that persons who fell in the year prior to the study (fallers) did not score significantly different on their outcome measures than non-fallers. Instead, persons with higher balance confidence scores had significantly higher scores on the mobility and social activity outcomes. The authors suggested that many lower limb prosthesis users expect to fall. In fact, just over half of the persons in the study (52%) reported a fall in the year prior to their participation in the study. The authors postulated that the expectation of falling may diminish the effects of actually falling on mobility and social activity outcomes. They also pointed out that some non-fallers have a fear of falling while some fallers do not fear falling (Tinetti et al., 1994 was cited). The authors suggest that training to improve the person's balance confidence could reduce their fear of falling and allow them to be more mobile and socially active. These improvements would likely lead to improved quality of life for lower limb prosthesis users. The appropriate design of the prosthetic ankle-foot system pursuant to the invention can also improve balance confidence in lower limb amputees. If achieved, the increased balance confidence could similarly lead to improved mobility, social activity, and quality of life.

Rockers have been used by many investigators to describe walking. Perry (1992) described the functions of the normal foot and ankle as creating three rockers to facilitate forward progression during walking: the heel, ankle, and forefoot rockers. Morawski and Wojcieszak (1978) studied the use of rockers in walking toys and suggested that rockers could be useful for the design of lower limb prostheses and orthoses. McGeer (1990) created mathematical and physical models of mechanisms that could walk down gentle slopes using only passive dynamic properties (i.e. without the use of external power). A key component of McGeer's model was the circular rocker used to replace the function of the foot and ankle. McGeer (1990) suggested that the "equivalent radius" for human walking would be roughly 0.3 times the length of the leg based on a simple model and calculation. Collins et al. (2005) have developed even more lifelike walking machines that incorporate rockers in place of the feet and ankles, and that are able to walk on level ground. Wisse and van Frankenhuyzen (2003) showed that increasing the radius of the rocker on a passive dynamic walking machine increases the amount of disturbance it can tolerate without falling down, demonstrating a clear relationship between rocker radius and walking stability. Adamczyk et al. (2006) recently examined the effects of wearing rocker boots on metabolic rate of able-bodied ambulators. Subjects were asked to walk at 1.3 m/s on a treadmill while wearing rigidankle walking boots connected to wooden rockers. The metabolic rate was calculated from respiratory gas exchange data measured during treadmill walking trials and was examined as a function of rocker radius. Adamczyk et al. (2006) reported that the subjects walked with a minimum metabolic rate when the rocker radius was approximately 0.3 times the leg length, matching the "equivalent radius" suggested by McGeer (1990). These studies suggest that rockers are important for robust and efficient bipedal ambulation.

Rockers are commonly used on walking casts and walking boots. Hullin and Robb (1991) studied eleven commercially available rockers for application to lower limb casts and found that only two gave walking characteristics that approached those of ablebodied walking. Both of these two attachable rockers were cams, but specific data regarding their radii were not presented. Milgram and Jacobson (1978) described many possible alterations for shoes to treat anomalies of the feet and ankles. A shoe with a constant radius rocker from heel to toe was said to provide an "ankle on the ground", suggesting that the effect of the ankle could be mimicked by the rocker for walking, eliminating the need for true ankle rotation. It is likely, however, that such a shoe would feel very unstable to its user during tasks that require standing and moderate swaying.

Knox (1996) examined static and dynamic mechanical properties of many prosthetic feet and stated that effective foot shape was key to their function for walking. Knox's work showed that the effective rocker shape of a prosthetic foot, which gradually develops as the foot deforms under the loading conditions of walking, affects the gait of its user. Knox (1996) developed a simple method for measuring the effective rocker shape of the ankle-foot system, and used the method to measure the rocker shapes (referred to later as "roll-over shapes") of both able-bodied and prosthetic ankle-foot systems. The Shape Foot was developed in applicants' laboratory in the 1990s and consists of a block of wood cut into a rocker shape that is made to attach to a lower limb prosthesis (Knox, 1996). The Shape Foot demonstrated that simple feet could be produced that would have good walking function if an effective rocker shape were used as a main design constraint. However, the Shape Foot was not good for standing.

Further work in applicants' laboratory led to the development of the Shape&Roll prosthetic foot, an inexpensive foot made of copolymer polypropylene/polyethylene that takes a biomimetic shape when loaded during walking (Sam et al., 2004). During development of the Shape&Roll prosthetic foot, questions arose concerning the specific effective rocker shapes that should be used in the design, particularly as amputees encounter different walking conditions in daily life. It was decided to examine the effective rockers used by able-bodied persons during walking and to consider these rockers as the gold standard for development of the Shape&Roll prosthetic foot.

Examinations in applicants' laboratory of able-bodied persons walking under a variety of conditions suggest that persons maintain similar effective rocker shapes during level walking. The effective rocker shape created by the foot and ankle together, the "anklefoot roll-over shape", appears to maintain the same general form and radius when persons walk at different speeds (Hansen et al., 2004a) and as persons walk with different amounts of weight added to their torso (Hansen, 2002; Hansen and Childress, 2005). The ankle-foot roll-over shape also changes in meaningful ways when women walk with shoes of different heel heights (Hansen and Childress, 2004): When wearing shoes with high heel heights, women adapted to more plantarflexed ankle positions, causing roll-over shapes to be translated downward. The combination of higher heels and increased ankle plantarflexion resulted in orientations of the roll-over shapes that were similar to those achieved when the women walked with lower heeled shoes. The apparent invariance of roll-over shape to level ground walking implies that it could be a useful and simple goal for design of ankle-foot prostheses and orthoses. Able-bodied persons utilize a circular rocker shape for walking on level terrain and maintain this same shape for walking at different speeds (Hansen et al., 2004a), when carrying different amounts of added weight (Hansen & Childress, 2005), or when using footwear of different heel heights (Hansen & Childress, 2004).

Recent studies of prosthesis alignment also support the importance of roll-over shape for level ground walking. Alignment of a prosthesis is the position and orientation of a prosthetic foot with respect to the residual limb socket, and is generally arrived at by a prosthetist using trial-and-error and adjustable hardware in the prosthesis. Our recent study of alignment indicated that experienced prosthetists adjust the alignments of various types of prosthetic feet, each having a different inherent roll-over shape based on mechanical properties, toward a single effective rocker shape with respect to the residual limb socket (Hansen et al., 2003). This finding suggests an "ideal" roll-over shape for walking that prosthetists inadvertently aim to mimic in a person's prosthesis. It seems that this "ideal" shape minimizes gait deviations and patient discomfort, and that is what the prosthetist attempts to find during the dynamic alignment process.

The bulk of previous work on rockers has focused on finding useful shapes for walking. However, for many elderly prosthesis users, standing balance may be equally or even more important.

SUMMARY OF THE INVENTION

The present invention provides a bi-modal ankle-foot prosthetic or orthotic device that provides a curved effective shape, such as for example a generally circular rocker (roll-over) shape, during walking and a flattened effective shape (relative to the curved shape) during standing. The bi-modal ankle-foot prosthetic or orthotic device includes an ankle piece and foot piece that cooperate to create a curved effective shape for walking and a flattened effective shape for standing, thereby mimicking the biological response of able-bodied persons during standing, swaying while standing, and walking.

An embodiment of the invention provides a bi-modal ankle-foot prosthetic or orthotic device that comprises a foot piece and a lockable ankle joint connected to the foot piece, the ankle joint and the foot piece and one or more resilient elements cooperating to provide a curved effective shape for walking when the ankle joint is unlocked and to provide a flattened foot shape for standing when the ankle joint is locked. For example, the foot piece cooperates with one or more resilient elements to provide a generally circular effective rocker (roll-over) shape for walking when the ankle joint is unlocked.

In an illustrative embodiment of the invention, a single-axis bi-modal ankle-foot prosthetic or orthotic device is provided and comprises a foot piece and a lockable ankle joint connected to the foot piece by a lockable pin joint in a manner to provide a flattened effective shape for standing. The lockable pin joint can include a pin or shaft whose axis of rotation is locked for the standing mode of use. With the ankle joint locked, the effective shape of the ankle-foot device takes that of the foot (i.e. a flattened shape) for standing including swaying while standing. With the ankle joint unlocked, the stiffness of the released ankle joint is set by one or more resilient bumper or springs elements that cooperate with the foot piece to achieve the appropriate curved effective rocker (roll-over) shape for walking.

The present invention provides a bi-modal ankle-foot prosthetic or orthotic device that offers two modes of function at the ankle for standing and walking. Providing a flattened effective shape in standing establishes an inherently stable base for these individuals and may reduce the occurrence of falls. This feature is quite advantageous since the majority of lower limb prosthesis users in industrialized nations are in the lowest functional levels and many had their amputations as a result of diabetes or vascular disease, Many of these users are older and have balance issues. Loss of sensation due to their systemic disease is also common. Falling is common in this group of prosthesis users. Providing a flattened effective shape in standing provides a stable base for these individuals and may reduce the occurrence of falls.

Other advantages and benefits of the present invention will become more readily apparent from the following detailed description taken with the following drawings.

BRIEF DESCRIPTION OF THE DRAWINGS

FIG. 5a is a schematic view of one embodiment of the ankle joint with a wrap spring clutch, while FIG. 5b is a schematic view of another embodiment of the ankle joint with a wrap spring clutch.

FIG. 6a is a schematic view of a locked ankle joint using a wrap spring clutch actuated by a cam and Bowden cable, while

FIG. 7a is a schematic elevation of the ankle-foot device with the cover body omitted to reveal the internal ankle joint and foot piece components with the ankle joint locked, while FIG. 7b is similar but showing the unlocked ankle joint.

FIG. 8c is a sectional view along line 8c-8c of FIG. 8a showing the ankle joint components and an electric motor to lock/unlock the ankle joint.

FIG. 9a is a schematic elevation of another embodiment of the ankle-foot device of the invention with the cover body and shoe broken away to reveal the internal ankle joint and foot piece components with the ankle joint locked. FIG. 9b is a sectional view along line 9b-9b of FIG. 9a showing the ankle joint components and an electric motor to lock/unlock the ankle joint, the shoe being omitted in FIG. 9b.

FIG. 10a is a schematic elevation of another embodiment of the ankle-foot device of the invention with the cover body omitted to reveal the internal ankle joint and foot piece components with ankle joint locked. FIG. 10b is a similar elevation of the ankle-foot device of FIG. 10a but showing the unlocked ankle joint.

DETAILED DESCRIPTION OF THE INVENTION

The present invention provides a bi-modal ankle-foot prosthetic or orthotic device that provides a curved effective shape, such as for example a generally circular rocker (roll-over) shape, during walking and a flattened effective shape (relative to the curved shape) during standing. In particular, applicants have examined the effective rocker (roll-over) shape of the able-bodied ankle-foot system during standing and low amplitude swaying and have found that this effective shape is very flat for standing including swaying. Thus, the ankle-foot device pursuant to the invention mimics its physiologic counterpart by conforming to a curved effective shape during walking and a flattened effective shape during standing and offers two modes of function at the ankle joint with one mode for standing and one mode for walking.

The present invention embodies observations of a 25 year old able-bodied female subject and others who participated in a pilot study to indicate the effective rockers used during walking, standing, and swaying. A modified Helen Hayes marker set (Kadaba et al., 1990) was placed on the subject. For each of the tasks, the subject's center of pressure of the ground reaction force was transformed from a laboratory-based coordinate system to a body-based coordinate system. The bodybased coordinate system was created in the sagittal plane using the ankle marker as the origin. The y-axis of the body-based coordinate system went from the ankle and through a virtual hip marker (sagittal projections of these markers). The x-axis went through the ankle, was perpendicular to the y-axis, and also remained in the sagittal plane. This method has been used by applicants to indicate the effective rocker, or rollover shape, that the physiologic knee-ankle-foot system conforms to during walking (Hansen et al., 2004a; Hansen et al., 2004b; Hansen and Childress, 2004; Hansen and Childress, 2005).

The female subject was asked to walk at her freely-selected walking speed while kinematic and kinetic data were collected. After the walking trials, the subject was asked to stand quietly for at least 10 seconds while data were collected. The subject was also asked to do small amplitude swaying in the anterior-posterior direction as well as large amplitude swaying (that required her to go up on her toes and heels) for at least 10 seconds per trial. The effective rockers that were calculated are shown in FIG. 2. The circles indicate the ankle marker, the origin of the leg-based coordinate system. Foot outlines are drawn for reference purposes and are not necessarily to scale. The effective rocker shapes ES that were calculated are shown in FIGS. 1a through 1d. The walking shapes (FIG. 1a) are curved shapes and look similar to knee-ankle-foot roll-over shapes previously reported for able-bodied ambulators (Hansen et al., 2004a).

Figure 1:
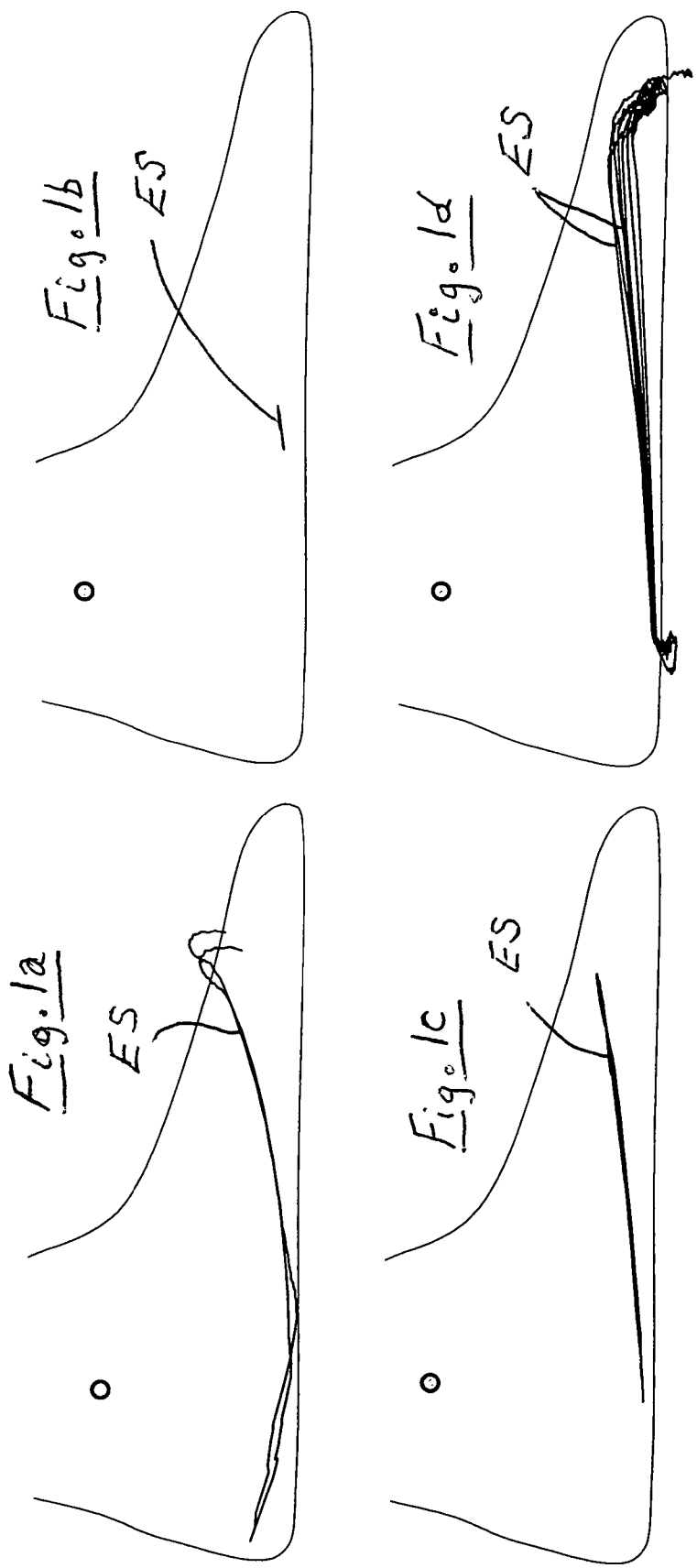
FIGS. 1a through 1d show effective rocker shapes during walking, FIG. 1a, during quiet standing, FIG. 1b, during low amplitude swaying, FIG. 1c, and during higher amplitude swaying, FIG. 1d. The circular markers indicate the ankle marker, which is the origin of the leg-based coordinate system. Foot outlines are drawn for reference purposes and are not necessarily to scale.
Figure 2:
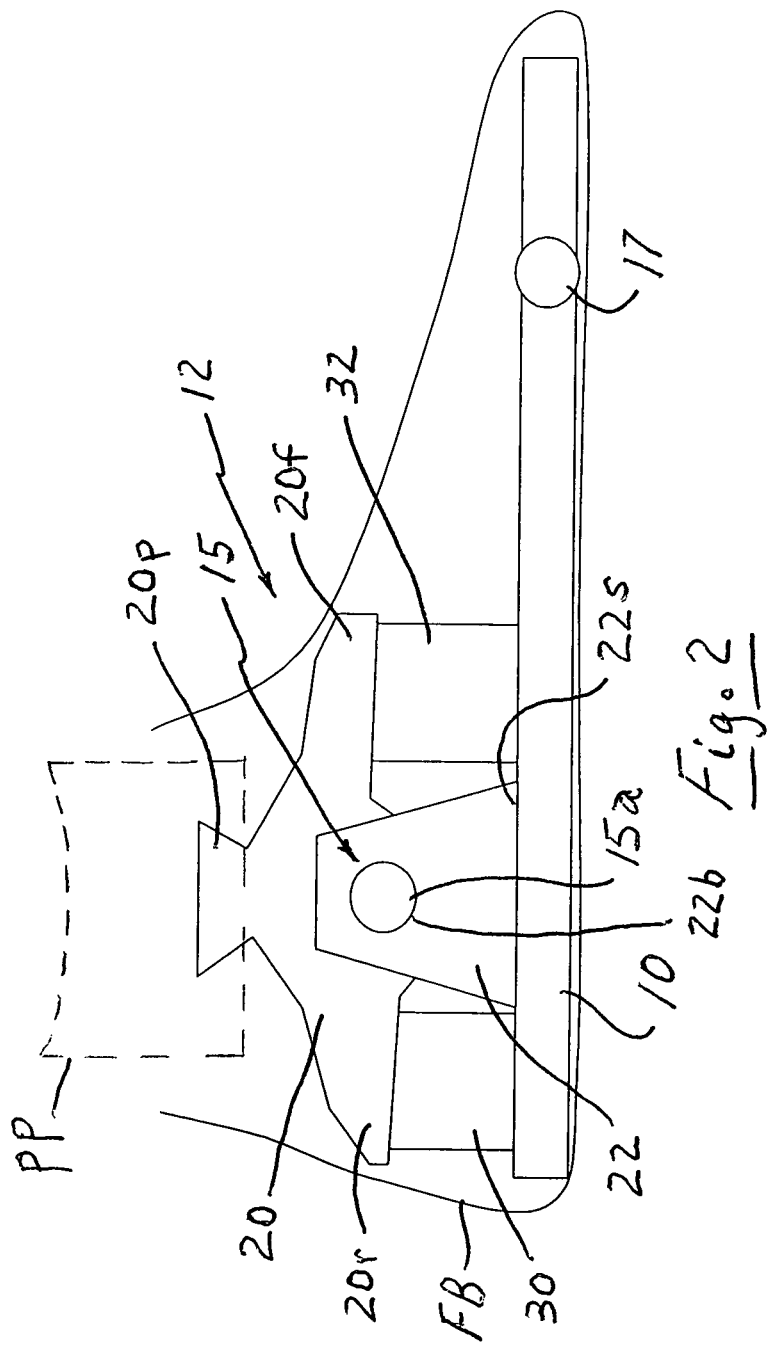
FIG. 2 illustrates an embodiment of an ankle-foot prosthetic device of the present invention. The ankle joint locking mechanism is hidden from view.

The effective shape measured during quiet standing is short and appears to be flat (FIG. 1b). When the subject did small amplitude swaying, a longer effective shape was seen that was also very flat (FIG. 1c). Finally, when the subject performed large amplitude swaying in which she went up on the heels and toes, the effective rocker is flat with downward dipping ends (see FIG. 1d). The effective rocker (roll-over) shapes shown for this subject indicate that the radii of these rocker shapes should be different for walking and standing. Creating a circular arc for walking and a flat shape for standing may be biomimetic.

Figure 7A:
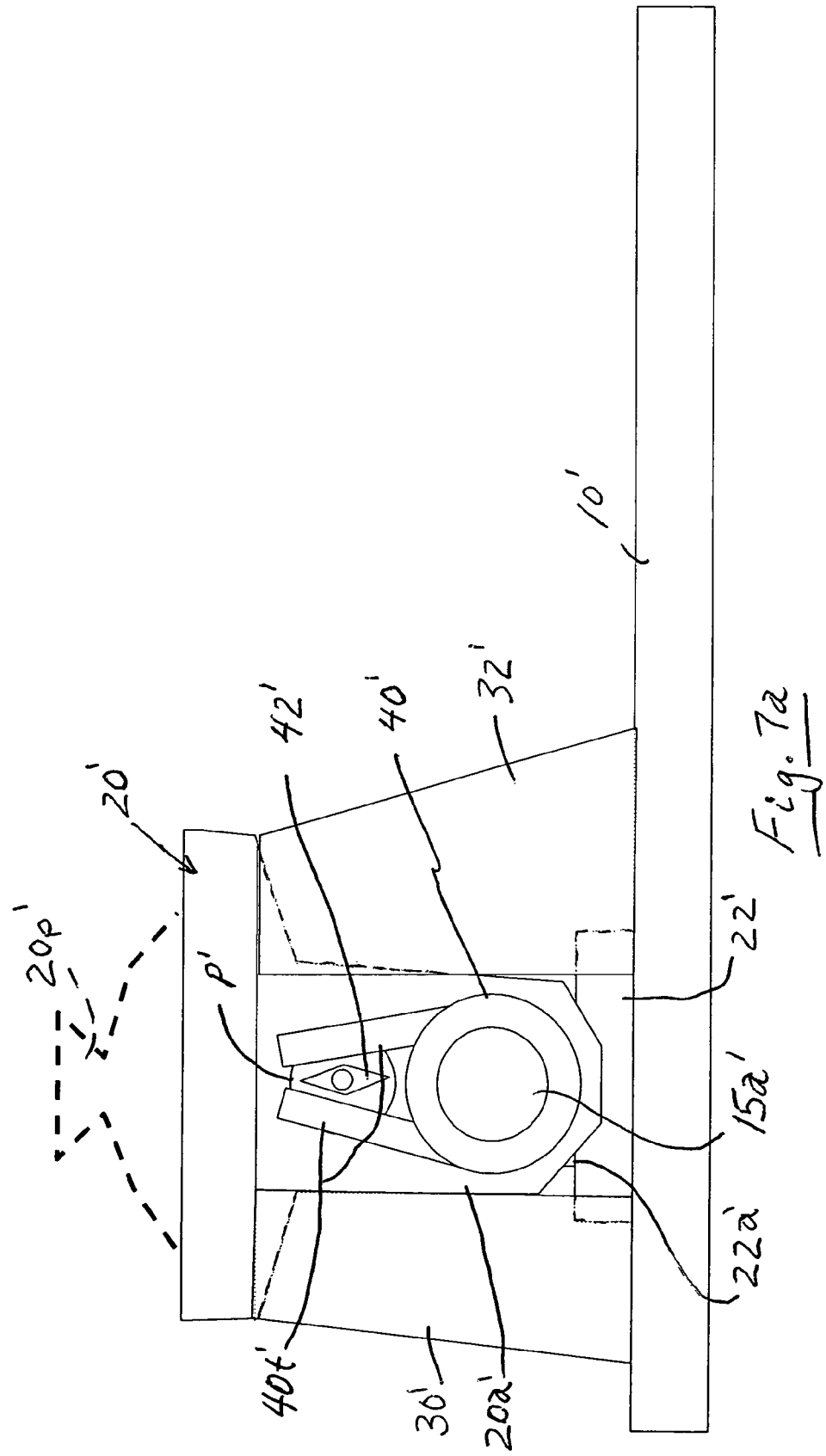
Figure 8A:
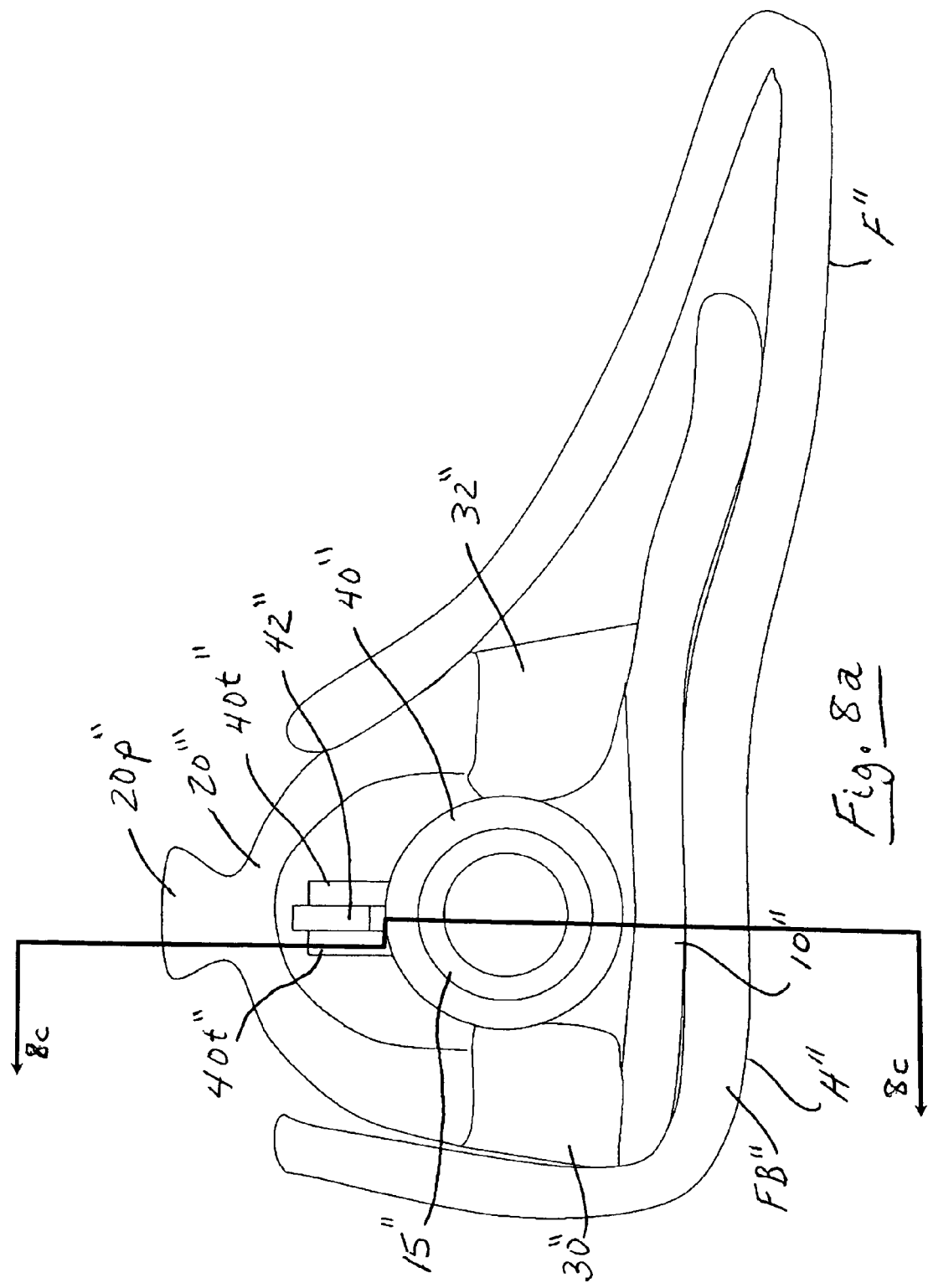
FIG. 8a is a schematic elevation of another embodiment of the ankle-foot device of the invention with the cover body broken away to reveal the internal ankle joint and foot piece components with the ankle joint locked.
Figure 8B:
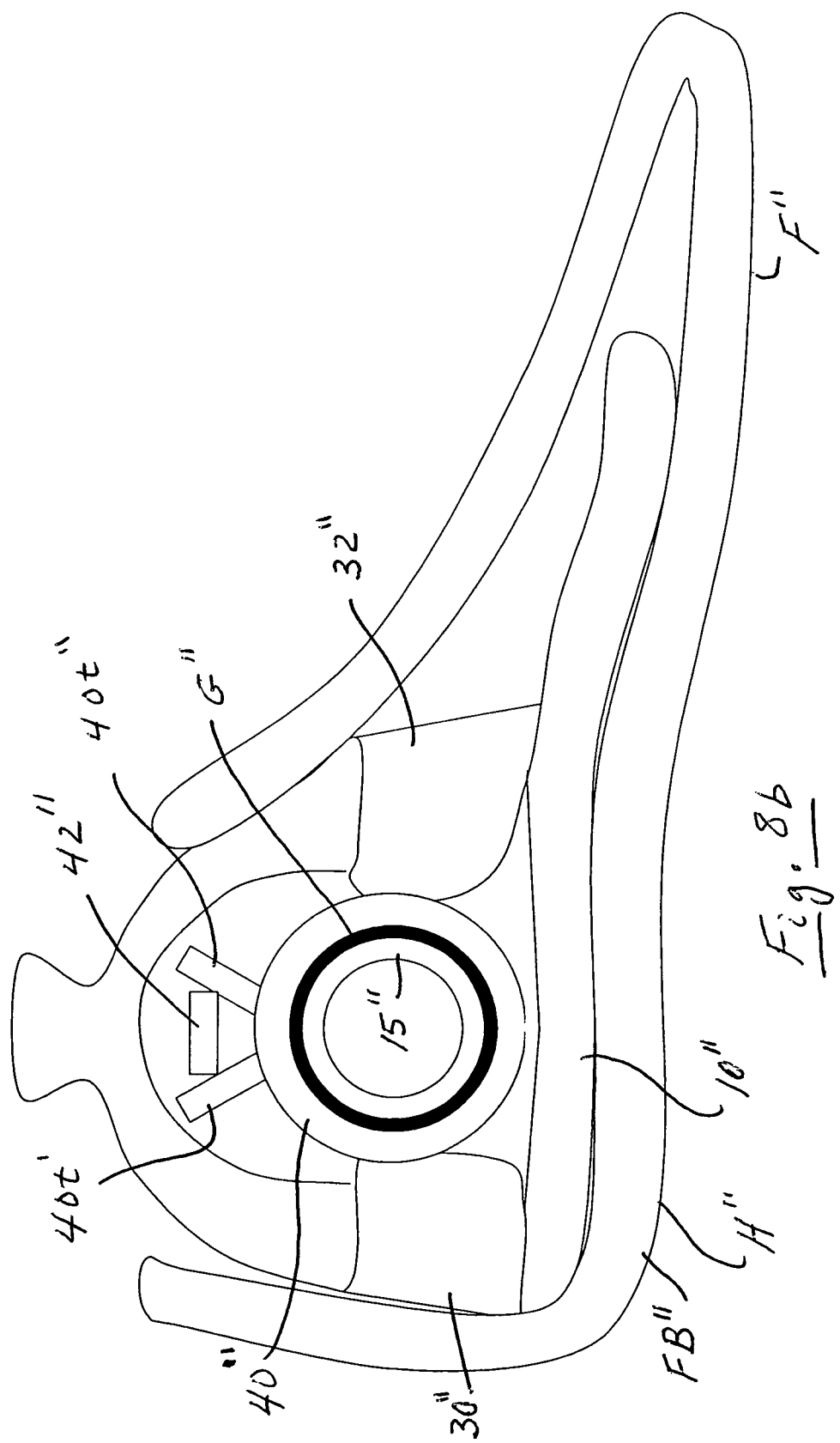
FIG. 8b is a similar elevation of the ankle-foot device of FIG. 8a but showing the unlocked ankle joint.

Further studies of the effective shapes of the ankle-foot system during walking, standing, and swaying have just been completed in the applicants' laboratory with similar results. The applicants measured effective ankle-foot rocker shapes used by eleven able-bodied persons during walking, swaying, and standing. The radius (measured as the inverse of the average curvature for the shape) was found to be about ⅓ of the leg length for walking, but over two times the leg length for swaying. The difference in curvature between walking and swaying shapes was highly significant (p=0.003). The foot piece 10 can comprise a flat rigid foot piece as shown in FIGS. 2 and 7a, 7b. Alternately, the foot piece 10 can comprise an arched bendable foot piece where the foot piece is arched upward contacting the heel and forefoot only as shown in FIGS. 8a, 8b with a surface of floor or ground. The foot piece 10 also can be any rigid or bendable shape that cooperates or combines with a shoe to provide a flattened effective shape as shown in FIG. 9a.

Pursuant to an illustrative embodiment of the invention shown in FIG. 2, an ankle-foot prosthetic or orthotic device is provided to provide the bi-modal function of having a curved effective shape (e.g. circular arc rocker or roll-over shape of FIG. 1a) for walking and a flattened effective shape (FIGS. 1b-1d) for standing including swaying. The device comprises a rigid foot piece 10 and a lockable ankle joint 12 connected to the foot piece in a manner to provide a flattened effective foot shape for standing, FIG. 2. The foot piece 10 and ankle joint 12 typically reside within an artificial and cosmetic foot-shaped body FB made of plastic or other material. With the ankle joint locked, the effective shape of the ankle-foot device takes that of the foot (i.e. a flattened foot shape) for standing including swaying while standing. With the ankle joint unlocked, the stiffness of the ankle joint is determined or set by one or more resilient bumper or spring elements 30, 32 described below to achieve the appropriate effective rocker foot shape for walking.

The ankle-foot prosthetic or orthotic device shown in FIG. 2 includes a lockable pin ankle joint 15 that connects an upper shank connector element 20 and lower foot connector elements 22. The rotatable pin (shaft) 15 has a lockable axis of rotation. The pin 15a can be cylindrical in shape and be made of steel or other suitable material. The upper shank connector element 20 includes depending flanges 20a having crossbores 20b that receive the pin 15a of the pin joint and an upper projection 20p shown as a dovetail type projection to connect to a pylon PP, which in turn would connect to a residual limb socket (not shown) of a lower limb. The lower foot connector elements 22 include cross-bores that receive the pin 15a and bottom surfaces 22s connected to the foot piece 10. The bottom surface 22s can be connected to the foot piece 10 by welding or fasteners. Alternately, the foot connector elements 22 and the foot piece 10 can be made as one-piece so that the connector elements 22 are integral with and part of the foot piece. The foot piece can be made of stiff, but lightweight plastic material, such as Delrin or nylon plastic, a composite structure, such as a carbon fiber-epoxy composite, or other suitable material. The foot piece 10 can incorporate an optional joint 17, such as flexural hinge, at the metatarsophalangeal level to allow "bending up of the toes" in the late stance phase of use of the foot piece. The connector elements 20 can be made of titanium, steel, or other suitable material.

Referring to FIGS. 5a and 5b, different configurations of the connector elements 20 and 22 are illustrated for purposes of illustration and not limitation. For example, the shank connector element 20 can have a configuration of downwardly facing clovis or U-shaped shank received outside of an upstanding connector elements 22, FIG. 5a. Alternately, the shank connector element 20 can have a configuration of a downwardly facing clovis or shank received inside of an upstanding connector elements 22, FIG. 5b. Other configurations of the connector elements 20, 22 are also possible.

The foot-ankle device includes one or more resilient elements such as a resilient heel bumper or spring 30 and a resilient forefoot bumper or spring 32 placed between the upper connector element 20 and foot piece 10 to provide ankle joint impedance necessary to provide an appropriate rocker (roll-over shape) for walking. The lockable ankle joint of the illustrative device allows a flattened effective shape to be provided for standing. Connector element 20 can include rear and forward projections 20r and 20f under which the heel and forefoot bumper or spring 30 and 32, respectively, are disposed.

The resilient elements 30, 32 can comprise rubber bumpers or can comprise steel compression springs, or other resilient elements. In any case, both the foot piece 10 and connector element 20 can have indentions that match the lower and upper geometries of the resilient elements 30, 32 to keep them contained and in place during operation of the ankle-foot device. Another alternative involves use of a one-piece resilient element, such as one-piece rubber bumper, that slides through the ankle joint (e.g. under the wrap spring clutch 40 described below). In that embodiment, frictional engagement of the rubber bumper with the wrap spring clutch 40 under the springs thereof would help to keep the bumper from sliding out on either end of the foot piece 10. A containment volume or edges on the connector element 20 may still be needed perhaps to contain the bumper on the shank member.

Determining the Appropriate Bumpers (Springs) for Use During Walking:

During walking, the individual's body interacts with the ground, creating a ground reaction force against the foot. For slow walking, the ground reaction force ramps from zero to body weight (during transfer of load between legs), stays at body weight during swing phase of the opposite foot, and ramps back down to zero as the load is transferred to the other leg (Perry, 1992). If this force profile is assumed, we can think of a body weight force vector moving along the bottom of the foot, increasing its moment arm about the ankle as it moves forward (see FIG. 3). The increased moment arm will create increases in forces experienced by the bumper and subsequent increases in deflections of the bumper. For a given moment arm, x, of the ground reaction force, we can indicate the deflections, d, we would like to have based on a radius of curvature, R, of the desired ankle-foot roll-over shape:

$$d = R - \sqrt{R^2 - x^2} \quad (1)$$

Figure 3:
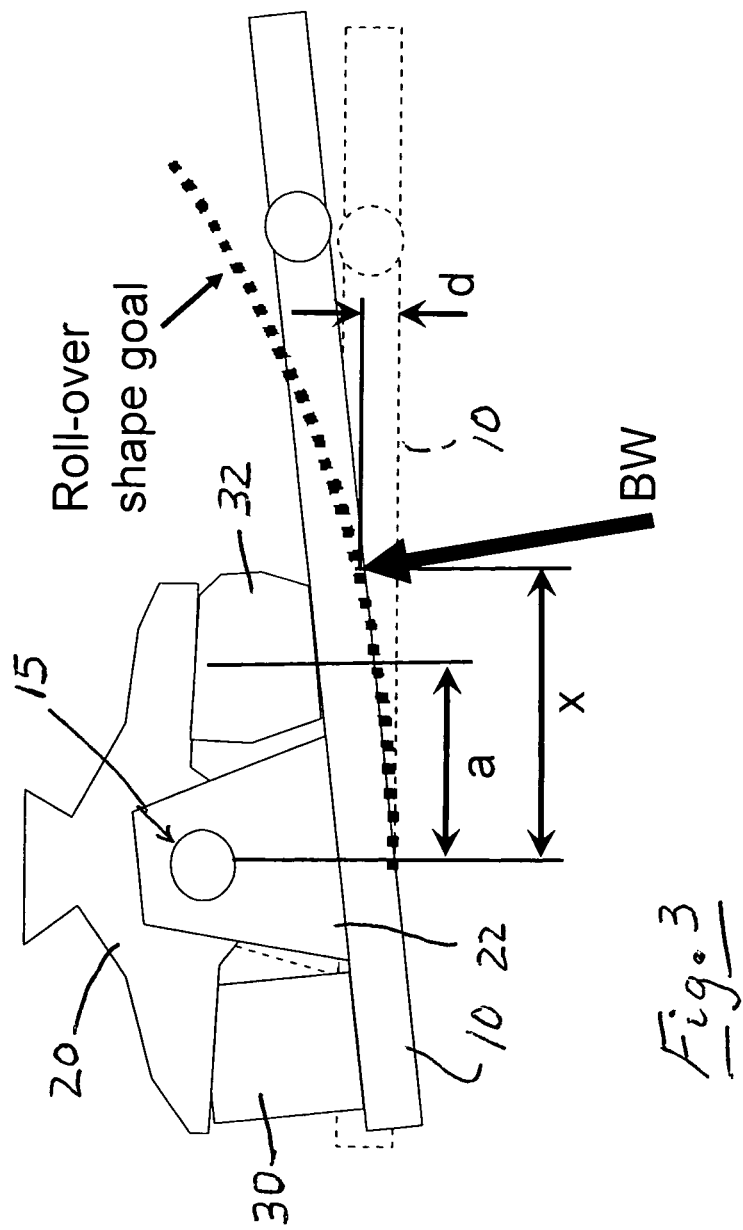
FIG. 3 is diagram used to describe bumper (spring) design. The dashed diagram indicates the unloaded system.

Equation 1 describes the lower arc of a circle. The approximate force at the forefoot bumper 32 is the ratio of the moment arms times the body weight BW:

$$F_{bumper} \approx BW(x/a) \quad (2)$$

where x and a are shown in FIG. 3.

Similarly, the approximate deflection of the forefoot bumper 32 will be related to the ratio of moment arms:

$$d_{bumper} \approx d(a/x) \quad (3)$$

Substituting Equation (1) into equation (3), we can find the deflection of the bumper in terms of the desired radis (R), the moment arm of the ground reaction force (x), and the moment arm of the bumper (a):

$$d_{bumper} \approx \left(R - \sqrt{R^2 - x^2}\right)\left(\frac{a}{x}\right) \qquad (4)$$

Figure 4:
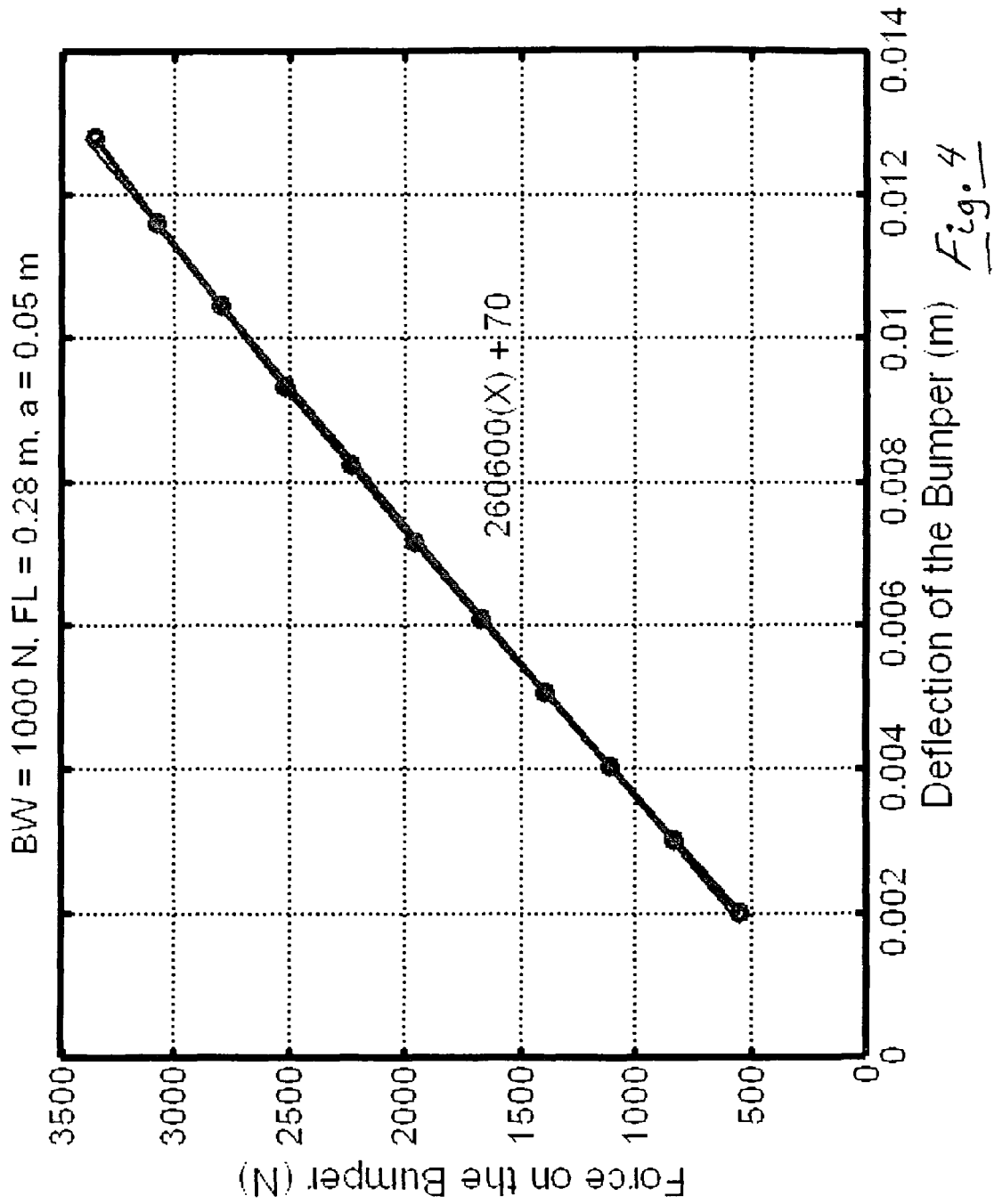
FIG. 4 is a plot of force versus deflection curve for a forefoot bumper that would yield a biomimetic ankle-foot roll-over shape.

From our studies of effective foot length in able-bodied persons (Hansen et al., 2004c), we know that the ground reaction force can only progress to the metatarsophalangeal level during single limb support. Also, we have found that the effective foot length ratio, the fraction of the foot that is effectively used in taking a step, is about 0.85 (including all of the heel section). The heel section comprises roughly 0.25 times the foot length, leaving 0.6 times the foot length in the forefoot. Therefore, we can assume that x starts just above zero (to avoid divide-by-zero issues with Equation 4) and goes to a distance of 0.6 times the foot length of interest. The moment arm of the bumper can be chosen, within reason, by the designer. The radius of the effective rocker should be approximately 19% of the person's height (Hansen, 2002), or roughly 125% of the foot length. Assuming a body weight of 1000 Newtons, a foot length of 0.28 meters, and a bumper moment arm (a) of 0.05 meters, we can create the desired force versus deflection curve for the ideal bumper (see FIG. 4). The relationship for this bumper appears to be linear and a best-fit curve yields a slope of 260,600 Newtons/meter, the desired stiffness of the bumper. The heel bumper element 30 can be designed using similar principles.

The bumper design has been explained assuming loading that would occur at slow speeds. At faster speeds, the loads fluctuate above and below the person's body weight in a double bump pattern (Perry, 1992). To avoid getting a smaller radius when walking faster, the ankle-foot system could have a hard stop (not shown) at the maximum deflection of the bumper when body weight of the user is applied to the metatarsophalangeal break location (i.e. the highest deflection on the curve in FIG. 4). This hard stop should allow the person to acquire a similar roll-over shape regardless of walking speed.

Pin Joint Locking Mechanism:

During balanced quiet standing; i.e., equal weight on each leg, the ankle experiences a load of approximately half body weight. Additionally, the ground reaction force is roughly in the middle of the foot (see FIG. 1B), giving a moment arm of roughly 0.25 times the length of the foot. However, the maximum torque that might be experienced by the ankle in its locked position would be expected when a person is perturbed toward the prosthetic side, causing all of their body weight to shift to the prosthesis and out to the metatarsophalangeal break (roughly 0.6 times foot length from the ankle). Therefore, the torque requirement of the locking mechanism is expected to be:

$$T=0.6(BW)(FL)$$

where BW is body weight and FL is foot length. We will multiply this value by a safety factor of 1.5 to increase the confidence in locking under most "normal" conditions. The safety factor is relatively small, acknowledging the importance of keeping the weight of the device to a minimum.

One locking mechanism that can be used for releasably locking the ankle is a wrap spring clutch 40 (see FIG. 5a, 5b) of the type previously used in a prosthetic elbow. The wrap spring clutch has two springs 40a and 40b that wrap in opposite directions on pin 15a. Each of the springs 40a and 40b has a control tang 40t that can be pushed in a direction to release the spring's grip on the pin 15a. The pin 15a can have a diameter that is slightly greater than the inside wrap diameter (hole) of the wrap springs to allow the springs to grip the joint pin 15a when a cam 42 is aligned vertically. The joint pin 15a can be rigidly connected to either the shank, FIG. 5a, or foot piece, FIG. 5b, and the wrap springs can be attached to the other.

Figure 6B:
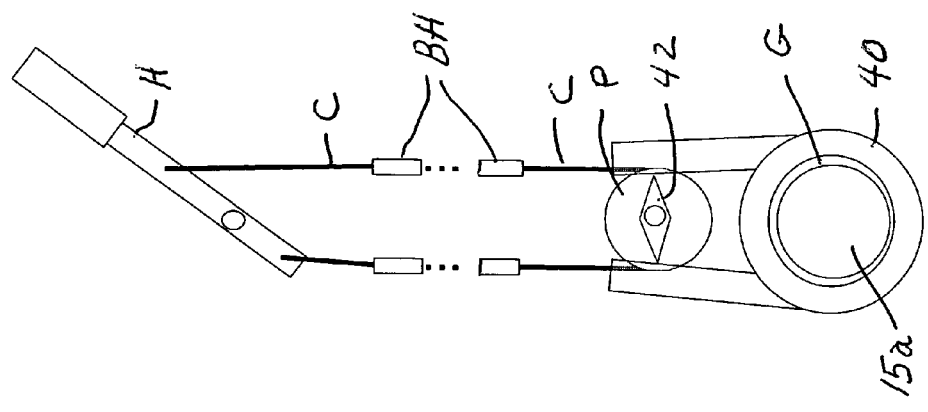
FIG. 6b is a schematic view of an unlocked ankle joint using a wrap spring clutch actuated by a cam and Bowden cable.
Figure 6A:
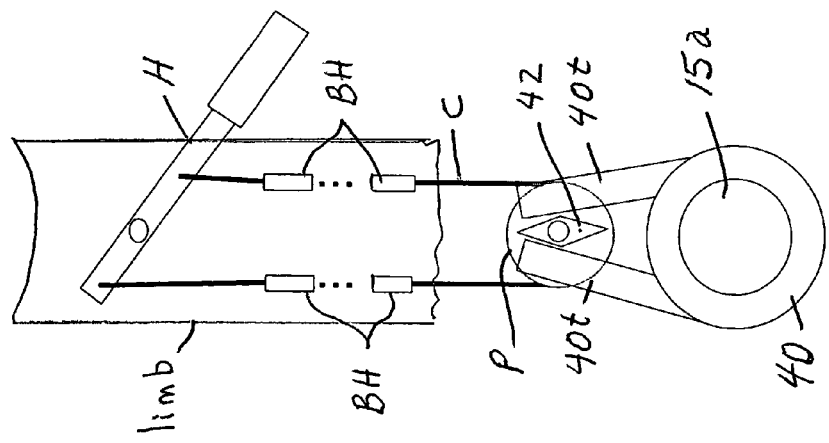

An oblong cam 42, FIGS. 6a, 6b, rotates under voluntary control of the individual user to either push the control tangs of the springs outward to loosen their grip on the rotatable pin 15a or to remove forces on the control tangs to allow the springs to grip the pin 15a. The voluntary control of the cam 42 is managed by a Bowden cable C as shown in FIGS. 6a, 6b which wraps around and rotates a pulley P on which the cam 42 is mounted. The pulley P can be mounted on the foot piece or shank piece for rotation in opposite directions by engagement with the Bowden cable. Two Bowden cable housings BH extend from the ankle-foot device on the prosthetic limb near the top of the prosthetic limb socket as shown schematically in FIG. 6a, 6b. The Bowden cable C is connected to an actuating handle H (or mechanical switch) that can be mounted on the prosthetic limb socket or to a belt around the thigh or waist so that the individual user can lock, FIG. 6a, or unlock, FIG. 6b, the ankle joint locking mechanism depending upon whether the user wants to stand or walk. In FIG. 6a, the user locks the ankle joint by moving the handle or switch to place the cam 42 in the vertical position. In FIG. 6b, the user unlocks the ankle joint by moving the handle or switch to place the cam 42 in the horizontal position to provide a gap G between the wrap springs 40a and the pin 15a permit pin rotation.

Wrap spring clutch systems provide a compact means to resist high torques with few moving parts and excellent engagement speed and reliability. In the gripping direction, the theoretical torque limit of a wrap spring clutch is:

$$T \approx r^2 f(e^{2\pi N\mu} - 1) \qquad (6)$$

where r is the radius of the shaft, f is the force per unit length of the contact line of the spring on the shaft, N is the number of spring coils, and μ is the coefficient of friction (Wiebusch, 1939). From Equation 6, one can see that a spring with many coils can reach a high theoretical torque limit because this limit increases exponentially with this variable. Also, changes in radius of the shaft can also have large effects on the torque limit.

Referring to FIG. 5a, one illustrative embodiment of the invention provides that the pin 15a passes through anti-friction bearings B residing on connector elements 22 (as pillow blocks) and is fixedly connected to the shank connector element 20 so that the shank connector element 20 rotates with the pin 15a. The wrap springs 40a are fixedly connected at their ends to the connector elements 22 and thus the foot piece 10 by welds, fasteners, and/or mechanical encapsulation of the end tangs.

Referring to FIG. 5b, another illustrative embodiment of the invention provides that the pin 15a passes through anti-friction bearings B residing on depending flanges 20a of shank connector element 20 and is fixedly connected to the connector elements 22 and thus the foot piece 10. The wrap springs 40a are fixedly connected at their ends to the shank connector element flanges 20a by welds, fasteners, and/or mechanical encapsulation of the end tangs.

Thus, the pin 15a can be fixedly connected to either the shank connector element 20 or the foot piece 10 via connector elements 22. The wrap springs 40a can be fixedly attached to the connector element(s) that is not connected to the pin 15a.

When the cam 42 (shown as the diamond shape cam in FIGS. 6a, 6b) is turned so that it is aligned horizontally (FIG. 6b), the springs 40a will be spread and allow rotation of the pin 15a with respect to the foot piece 10 during walking. The bearings B allow rotation of the pin 15a when the springs are spread. Rotation of the cam 42 to the position of FIG. 6a will lock the ankle joint (i.e. the lock the axis of rotation of pin 15a) during standing.

If the wrap spring clutch 40 cannot be made to withstand the torque requirements using a reasonable mass, other alternatives can include, but are not limited to, conventional pin-locking and internal/external gear-mating mechanisms. The wrap spring clutch is preferred over the other alternatives because it allows locking of the ankle joint over a continuous range of angles. This feature could allow a person to brake the ankle in a variety of positions, which could be useful for various tasks such as standing on sloped surfaces. The invention is not limited to practice using the wrap spring clutch locking mechanism described above and can be practiced using other mechanisms to lock the axis of rotation of the pin 15a. Also, the cam 42 can be rotated by a small motor or other actuator, rather than the Bowden cable system described.

A particular illustrative embodiment of the ankle-foot device is schematically shown in FIGS. 7a, 7b with one of the depending flangs 20a' of the upper connector element 20' omitted from the figure to reveal the pin locking mechanism. In FIGS. 7a and 7b, similar features and elements as described above for FIG. 2 through FIGS. 6a, 6b are represented by similar reference numerals primed. Between the upper connector element 20' and the foot piece 10', resilient bumpers 30', 32' are positioned and designed to provide the appropriate rocker (or roll-over) shape during walking. The wrap spring clutch 40' is disposed on the pin 15a' for releasably locking the axis of rotation of the pin 15a' and thus the upper connector element 20' and the foot piece 10' for the standing mode of use, providing a flattened effective shape for standing. The connector elements 20', 22' receive the pin 15a' in a manner similar to that shown in FIG. 5a or FIG. 5b to permit its rotation for the walking mode of use.

A diamond shaped cam 42' disposed on pulley P' is used to engage and disengage the wrap spring clutch 40'. This cam 42' can be rotated using the Bowden cable system described above and in a manner similar to that used in a conventional prosthetic elbow. Alternatively, the cam 42' can be turned using a small motor that is activated based on other signals from the body, e.g. EMG signals, or could be activated by pressing a small remote control similar to those used in locking and unlocking car doors. A set of sensors could be used to indicate whether the person is walking or standing.

There are many expected commercial applications for bi-modal ankle-foot prosthetic device of the invention. The primary application is in the development of prosthetic ankle-foot systems for lower limb prosthesis users. However, ankle-foot orthoses could also incorporate bi-modal functionality. Substantial ankle-foot orthoses with bi-modal function could be developed within the scope of the invention for persons with disabilities affecting the ankle-foot system and their balance. Less substantial ankle-foot orthoses may also be useful for the general population of elderly persons, many of whom have balance issues that can lead to falls and substantial reductions in quality of life. Lastly, ankle-foot systems with bi-modal functionality may be useful in the development of walking robots. Flat effective shapes would give these robots an inherently stable base (foot) during standing tasks, but allow them to walk with the ankle in the unlocked mode.

FIG. 8a is an elevation of another embodiment of the ankle-foot device of the invention wherein the foot piece 10" and a foot piece cover FB" provide an upwardly arched foot shape contacting the heel and forefoot with a floor or ground surface. The upwardly arched foot shape can be used without a shoe or with a shoe having a heel height that would match the upwardly arching shape (see FIG. 9a). With the appropriate shoe, the effective foot-shoe shape could be flat. The ankle joint is locked in FIG. 8a, while the ankle joint is unlocked in FIG. 8b. In FIGS. 8a and 8b, the cover body FB" is broken away to reveal internal ankle joint and foot piece components and one of the depending flangs 20a" of the upper connector element 20" is omitted from the figures to reveal the pin locking mechanism. Reference numerals double primed are used to designate similar ankle-foot device components as described and shown above.

The embodiment of FIGS. 8a, 8b, and 8c differs from that described above in having an upwardly arched foot piece 10" that includes upstanding flanges 10a" that receive the ends of a hollow joint pin 15a" of the ankle joint 15". The foot piece 10" is received in a foot-shaped cover body FB". The ankle joint is locked by wrap spring clutch 40" having control tangs 40t", which are allowed to close to lock the ankle joint or are opened by cam 42" actuated to spread apart the control tangs 40" to create gap G", FIG. 8b. Gap G" frees the ankle joint to cooperate with the foot piece to provide a curved (e.g. rocker) effective shape (FIG. 1a). The cam 42" is actuated to rotate relative to the control tangs 40t" by rotation of shaft S" of an electric motor M" disposed on the upper connector element 20" and controlled by the individual user or by sensors. When the ankle joint is locked (control tangs closed), a flattened effective shape (FIG. 1c-1d) is provided by the prosthetic device for standing.

FIGS. 9a and 9b illustrate still another embodiment of the ankle-foot device of the invention wherein reference numerals triple primed are used to designate similar ankle-foot device components as described and shown above. In FIG. 9a, the cover body FB'" and shoe are broken away and one of the flanges 20a'" and 10a"" of the upper connector element and foot piece are omitted to reveal internal ankle joint and foot piece components. The embodiment of FIGS. 9a, 9b differs from those described above in that the ankle-foot device employs foot piece 10'", a foot piece cover body FB'" that receives the foot piece, and a shoe that can cooperate to provide a curved effective shape for walking and a flattened effective shape for standing. The upwardly arched foot piece 10'" includes upstanding flanges 10a'" that nest in depending flanges 20a'" of upper connector element 20'" and receive the ends of a hollow joint pin 15a" of the ankle joint 15". The foot piece 10" is received in a foot-shaped cover body FB". The ankle joint is locked by wrap spring clutch 40'" having control tangs 40t'", which are allowed to close to lock the ankle joint or are opened by cam 42" actuated to spread apart the control tangs 40" to create a gap (not shown) that frees the ankle joint to cooperate with the foot piece to provide a curved (e.g. rocker) effective shape (FIG. 1a). The cam 42'" is actuated to rotate relative to the control tangs 40t'" by rotation of shaft S'" of an electric motor M'" disposed on the foot piece 10'" and controlled by the individual user or by sensors. When the ankle joint is locked (control tangs closed), a flattened effective shape (FIG. 1c-1d) is provided by the prosthetic device for standing.

Referring to FIGS. 10a, 10b, still another embodiment of the invention is illustrated. This embodiment comprises a rigid or bendable foot piece 110 connected to an upper connector element 120 by a simple flexural ankle joint 115 defined between joint slots 115s. The ankle joint 115 is locked to prevent flexing by locking blocks 150, 152 that are slid by a linear actuator (not shown) into the slots 115s of the flexural joint to this end. The locking blocks 150, 152 are disposed on the foot piece 110 and are held and slid in tracks or grooves thereon and held in the lock position by friction and/or the linear actuator that slides them along their tracks or grooves. When the flexural joint is unlocked, FIG. 10b, the flexural joint 115 and foot piece 110 cooperate to provide a curved (e.g. rocker) effective shape (FIG. 1a) of the prosthetic device for walking. When the flexural joint is locked, FIG. 10a, the prosthetic device provides a flattened effective shape (FIGS. 1b-1d) for standing.

Although the invention has been described with respect to certain embodiments for purposes of illustration, those skilled in the art will appreciate that changes and modifications can be made therein within the scope of the invention as set forth in the appended claims.

REFERENCES

Adamczyk, P. G., Collins, S H. and Kuo, A. D. (2006). The advantages of a rolling foot in human walking. J Exp Blot 209, 3953-3963.

Adams P F, Hendershot G E, and Marano M A. (1999). Current estimates from the National Health Interview Survey, 1996. National Center for Health Statistics. Vital Health Stat 10(200).

Collins, S., Ruina, A., Tedrake, R., Wisse, M. (2005). Efficient bipedal robots based on passive-dynamic walkers. Science 307, 1082-1085.

Galley, R. S., Roach, K. E., Applegate, E. B., Cho, B., Cunniffe, B., Lict, S., Maguire, M, and Nash, M. S_(2002). The amputee mobility predictor: an instrument to assess determinants of the lower-limb amputee's ability to ambulate. Arch Phys Med Rehabil 83, 613-627.

Gard, S. A, and Childress, D. S (2001). What determines the vertical displacement of the body during normal walking? J Prosthet Orthot 13, 64-67.

Hansen, A. H. (2002). Roll-over characteristics of human walking with applications for artificial limbs. Ph.D. thesis, Evanston, Northwestern University Hansen, A. H., Meier, M. R., Sam, M., Childress, D. S. and Edwards, M. L. (2003). Alignment of trans-tibial prostheses based on roll-over shape principles. Prosthet Orthot Int 27(2), 89-99.

Hansen, A. H, Childress, D. S., and Knox, E. H. (2004a). Roll-over shapes of human locomotor systems: effects of walking speed. Clin Biomech 19(4), 407-14.

Hansen, A. H., Childress, D. S., Miff, S. C. (2004b) Roll-over characteristics of human walking on inclined surfaces. Hum Movement Sci. 23(6), 807-821.

Hansen, A., Sam, M., Childress, D. (2004c) The Effective Foot Length Ratio (EFLR) A Potential Tool for Characterization and Evaluation of Prosthetic Feet. J Prosthet Orthot, 16(2), 41-45.

Hansen, A. H. and Childress, D. S. (2004). Effects of shoe heel height on biologic roll-over characteristics during walking. J Rehabil Res Dev 41(4), 547-554.

Hansen, A. H. and Childress, D. S. (2005) Effects of Adding Weight to the Torso on Roll-over Characteristics of Walking. J Rehabil Res Dev, 42(3), 381-390.

Hullin, M. G. and Robb, J. E. (1991). Biomechanical effects of rockers on walking in a plaster cast. J Bone Joint Surg Br 73(1), 92-5.

Jhoun, J. (1997), Studies of human standing, stepping, and gait initiation. Ph.D. thesis, Evanston, Northwestern University.

Kadaba, M. P., Ramakrishnan, H. K. and Wootten, M E. (1990). Measurement of lower extremity kinematics during level walking. J Orthop Res 8(3), 383-92.

Knox, E. H. (1996). The role of prosthetic feet in walking. Ph.D. thesis, Evanston, Northwestern University.

McGeer, T. (1990). Passive dynamic walking. Int J Robot Res 9(2), 62-82.

Meier, R. (1998) High Tech and the Active Older Amputee. Conference Book of the 9th World Congress of the International Society of Prosthetics and Orthotics, Amsterdam, The Netherlands Miff S C, Hansen A H, Childress D S, Gard S A, Meier MR. Roll-over Shapes of the Able-Bodied Knee-Ankle-Foot System during Gait Initiation, Steady-State Walking, and Gait Termination. Gait and Posture, in press.

Milgram, J. E. and Jacobson, M. A. (1978). Footgear: therapeutic modifications of sole and heel. Orthopaedic Review 7(11), 57-62.

Miller, W. C., Deathe, B., Speechley, M., and Koval. J. (2001). The influence of falling, fear of falling, and balance confidence on prosthetic mobility and social activity among individuals with a lower extremity amputation. Arch Phys Med Rehabil 82, 1238-1244.

Morawski, J. and Wojcieszak, I. (1978). Miniwalker—a resonant model of human locomotion. Biomechanics VIA. E. Asmussen, Jorgensen, K. Baltimore, University Park Press. 2A: 445-451.

Nashner, L. M. (2001). Computerized dynamic posturography. Practical Management of the Dizzy Patient Goebel, J. A., Philadelphia, Lippincot Williams & Wilkins. 143-170.

O'Loughlin, J. L., Robitaille, Y., Boivin, J., and Suissa S. (1993). Incidence of and risk factors for falls and injurious falls among the community-dwelling elderly. Am J Epidemiol 137, 342-354.

Owings M F, Kozak L J. (1998). Ambulatory and inpatient procedures in the United States, 1996. National Center for Health Statistics. Vital Health Stat 13(139).

Perry, J. (1992). Gait Analysis.: Normal and Pathological Function. Thorofare, SLACK Incorporated.

Sam, M., Childress, D. S., Hansen, A. H., Meier, M. R., Lambla, S., Grahn, E. C., Rolock, J. S (2004). The Shape&Roll prosthetic foot (Part 1): Design and development of appropriate technology for low-income countries. Med Confl Surviv 20(4), 294-306.

Sattin, R. W. (1992). Falls among older persons: A public health perspective. Annu Rev Publ Health 13, 489-508.

Soderberg, B., Wykman, A., Schaarschuch, R., Persson, B. M. (2001) Partial Foot Amputations: Guidelines to Prosthetic and Surgical Techniques. Second Edition. Swedish Orthopaedic Association's Publication Series No. 13. Helsingborg, Sweden.

Tinetti, M. E., Speechley, M., and Ginter, S. F. (1988). Risk factors for falls among elderly persons living in the community. N Engl J Med 319, 1701-1707.

Tinetti, M. E., and Speechley, M. (1989). Prevention of falls among the elderly. N Engl JMed 320, 1055-1059.

Tinetti, M. E., Mendes de Leon, C. F., Doucette, J. T., and Baker, D. I. (1994). Fear of falling and fall-related efficacy in relationship to functioning among community-dwelling elders. J Gerontol 49, M140-147.

Wiebusch, C. F. (1939) The Spring Clutch. Journal of Applied Mechanics, September, Al 03-Al 08.

Wisse, M. and van Frankenhuyzen, J. (2003). Design and Construction of MIKE; a 2D autonomous biped based on passive dynamic walking. Proceedings of the AMAM Conference Of Adaptive Motion of Animals and Machines, Kyoto, Japan.

The above listed references are incorporated herein by reference.

We claim:

1. A bi-modal ankle-foot device comprising: a pylon; a rigid foot piece; an ankle joint pivotably connecting the pylon to the foot piece so that the foot piece is rotatable relative to the pylon between plantarflexed and dorsiflexed positions; an ankle joint locking mechanism for releasably locking the ankle joint at any angular orientation of the foot piece to the pylon between the plantarflexed and dorsiflexed positions, the locking mechanism having both a standing mode of operation where the ankle joint is locked and a walking mode of operation where the ankle joint is unlocked; and an actuator for the locking mechanism controlled remotely from the ankle joint.

2. The device of claim 1 which provides a curved effective foot shape for walking determined by cooperation of the foot piece with one or more resilient elements when the joint is unlocked.

3. The device of claim 2 wherein the curved effective shape comprises a circular rocker foot shape.

4. The device of claim 2 wherein the one or more resilient elements reside between the foot piece and an upper shank connector element that is connected to the pylon.

5. The device of claim 1 that includes a rotatable pin at the ankle joint and rotation of the pin is locked for standing.

6. The device of claim 5 wherein a shank connector element is connected to a foot connector element by a pin joint having the pin.

7. The device of claim 5 wherein the locking mechanism locks rotation of the pin.

8. The device of claim 7 wherein the locking mechanism comprises a wrap spring clutch disposed on the pin to lock the pin joint for standing.

9. The device of claim 8 including a cam between control tangs of the wrap clutch spring.

10. The device of claim 9 wherein the cam spreads the control tangs to unlock the pin axis of rotation and the cam allows the control tangs to close to lock the pin.

11. The device of claim 9 wherein the cam is controlled by an actuator cable.

12. The device of claim 1 wherein the locking mechanism further comprises a cable and a handle connected to the cable and configured to be controlled by the wearer of the device to selectively engage or disengage the locking mechanism.

13. The device of claim 1 wherein the actuator comprises a motor for controlling the locking mechanism wherein the motor is controlled in response to user switch input or to sensor input.

14. The device of claim 1 wherein the locking mechanism comprises a slidable locking block disposed on the rigid foot piece that is slidable relative to the ankle joint to lock or unlock the ankle joint.

15. The device of claim 1 wherein the ankle joint locking mechanism is wearer-operable to permit the wearer to select the angular orientation of the foot piece to the pylon at which the ankle joint is locked.

16. The device of claim 1 wherein the bi-modal ankle-foot device further comprises a shank connector element fixed to the pylon, a foot connector element fixed to the rigid foot piece, a in pivotably connecting the shank connector element to the foot connector element, and a resilient bumper interposed between the shank connector element and the rigid foot piece to provide resistance to rotation of the shank connector element relative to the foot connector element, the resilient bumper having a first surface engaging the shank connector element and a second surface engaging the rigid foot piece.

17. The device of claim 16 wherein the shank connector element comprises forward and rearward projections and the resilient bumper comprises separate first and second members, the first member being interposed between the foot piece and the forward projection of the shank connector element and the second member being interposed between the foot piece and the rearward projection of the shank connector element, each of the first and second members of the resilient bumper having a first surface respectively engaging the forward and rearward projections of the shank connector element and a second surface engaging the rigid foot piece, the forward and rearward projections of the shank connector element each having a first indentation shaped to receive the first surface of the associated first or second member of the resilient bumper and the foot plate having a second indentation shaped to receive the second surfaces of the first and second members of the resilient bumper.

18. A bi-modal ankle-foot prosthetic or orthotic device comprising: a pylon; a rigid foot piece; an ankle joint pivotably connecting the pylon to the foot piece so that the foot piece is rotatable relative to the pylon between plantarflexed and dorsiflexed positions; an ankle joint locking mechanism for releasably locking the ankle joint at any angular orientation of the foot piece to the pylon between the plantarflexed and dorsiflexed positions in response to user or sensor input, the locking mechanism having both a standing mode of operation where the ankle joint is locked and a walking mode of operation where the ankle joint is unlocked; and an actuator for the locking mechanism controlled remotely from the ankle joint.

19. The device of claim 18 which provides a curved effective shape for walking determined by cooperation of the foot piece with one or more resilient elements when the ankle joint is unlocked.

20. The device of claim 19 wherein the one or more resilient elements reside between the foot piece and an upper shank connector element that is connected to an artificial limb.

21. The device of claim 18 that includes a rotatable pin at the ankle joint and rotation of the pin is locked for standing.

22. The device of claim 21 wherein the ankle joint comprises a shank connector element connected to foot connector element by the pin.

23. The device of claim 22 including a cam between control tangs of the wrap clutch spring.

24. The device of claim 23 wherein the cam is operated controlled by an actuator cable.

25. The device of claim 21 including a wrap spring clutch disposed on the pin to lock rotation of the pin for standing.

26. The device of claim 25 wherein the cam spreads the control tangs to unlock the pin to permit rotation and allows the control tangs to close to lock the pin to prevent rotation.

27. The device of claim 18 wherein the locking mechanism comprises a slidable locking block disposed on the rigid foot piece that is slidable relative to the ankle joint to lock or unlock the ankle joint.

28. The device of claim 18 wherein the bi-modal ankle-foot prosthetic or orthotic device further comprises a shank connector element fixed to the pylon, a foot connector element fixed to the rigid foot piece, a in pivotably connecting the shank connector element to the foot connector element, and a resilient bumper interposed between the shank connector element and the rigid foot piece to provide resistance to rotation of the shank connector element relative to the foot connector element, the resilient bumper having a first surface engaging the shank connector element and a second surface engaging the rigid foot piece.

29. The device of claim 28 wherein the shank connector element comprises forward and rearward projections and the resilient bumper comprises separate first and second members, the first member being interposed between the foot piece and the forward projection of the shank connector element and the second member being interposed between the foot piece and the rearward projection of the shank connector element, each of the first and second members of the resilient bumper having a first surface respectively engaging the forward and rearward projections of the shank connector element and a second surface engaging the rigid foot piece, the forward and rearward projections of the shank connector element each having a first indentation shaped to receive the first surface of the associated first or second member of the resilient bumper and the foot plate having a second indentation shaped to receive the second surfaces of the first and second members of the resilient bumper.

30. A method of controlling mode of movement of an ankle-foot joint comprising a pylon, a rigid foot piece, an ankle joint pivotably connecting the pylon to the foot piece so that the foot piece is rotatable relative to the pylon between plantarflexed and dorsiflexed positions, an ankle joint locking mechanism for releasably locking the ankle joint at any angular orientation between the plantarflexed and dorsiflexed positions, and an actuator for the locking mechanism controlled remotely from the ankle joint, the method comprising controlling the ankle joint locking mechanism in response to user or sensor input to both unlock the ankle joint to enable it to cooperate with a foot piece for walking and lock the ankle joint for standing.

31. The method of claim 30 wherein the ankle-foot device further comprises a shank connector element fixed to the pylon, a foot connector element fixed to the rigid foot piece, a in pivotably connecting the shank connector element to the foot connector element, and a resilient bumper interposed between the shank connector element and the rigid foot piece to provide resistance to rotation of the shank connector element relative to the foot connector element, the resilient bumper having a first surface engaging the shank connector element and a second surface engaging the rigid foot piece.

32. The method of claim 31 wherein the shank connector element comprises forward and rearward projections and the resilient bumper comprises separate first and second members, the first member being interposed between the foot piece and the forward projection of the shank connector element and the second member being interposed between the foot piece and the rearward projection of the shank connector element, each of the first and second members of the resilient bumper having a first surface respectively engaging the forward and rearward projections of the shank connector element and a second surface engaging the rigid foot piece, the forward and rearward projections of the shank connector element each having a first indentation shaped to receive the first surface of the associated first or second member of the resilient bumper and the foot plate having a second indentation shaped to receive the second surfaces of the first and second members of the resilient bumper.

* * * * *